US008900154B2

(12) United States Patent
Stahmann et al.

(10) Patent No.: US 8,900,154 B2
(45) Date of Patent: Dec. 2, 2014

(54) PREDICTION OF THORACIC FLUID ACCUMULATION

(75) Inventors: Jeffrey E. Stahmann, Ramsey, MN (US); Quan Ni, Shoreview, MN (US); Jesse W. Hartley, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1497 days.

(21) Appl. No.: 11/136,195

(22) Filed: May 24, 2005

(65) Prior Publication Data

US 2006/0271116 A1 Nov. 30, 2006

(51) Int. Cl.

| | |
|---|---|
| ***A61B 5/08*** | (2006.01) |
| ***A61B 5/053*** | (2006.01) |
| *A61N 1/362* | (2006.01) |
| *A61N 1/05* | (2006.01) |
| *A61N 1/365* | (2006.01) |

(52) U.S. Cl.

CPC ............. *A61B 5/0537* (2013.01); *A61B 5/0538* (2013.01); *A61N 1/3627* (2013.01); *A61N 2001/0585* (2013.01); *A61N 1/365* (2013.01)

USPC .......................................................... 600/484

(58) Field of Classification Search

USPC .......................................................... 600/484

See application file for complete search history.

(56) References Cited

U.S. PATENT DOCUMENTS

| | | | |
|---|---|---|---|
| 4,059,169 | A | 11/1977 | Hagen |
| 4,450,527 | A | 5/1984 | Sramek |
| 4,567,892 | A | 2/1986 | Plicchi et al. |
| 4,576,183 | A | 3/1986 | Plicchi et al. |
| 4,686,987 | A | 8/1987 | Salo et al. |
| 5,003,976 | A | 4/1991 | Alt |
| 5,036,849 | A | 8/1991 | Hauck et al. |
| 5,273,034 | A | 12/1993 | Nilsson |

(Continued)

FOREIGN PATENT DOCUMENTS

| | | | |
|---|---|---|---|
| EP | 0584388 | A1 | 3/1994 |
| EP | 0620420 | | 10/1994 |

(Continued)

OTHER PUBLICATIONS

"International Search Report and Written Opinion for Application No. PCT/US2006/019937, date mailed Dec. 12, 2006", 14 Pages.

(Continued)

*Primary Examiner* — Michael D'Angelo
*Assistant Examiner* — Christian Jang
(74) *Attorney, Agent, or Firm* — Schwegman Lundberg & Woessner, P.A.

(57) ABSTRACT

This patent document discusses, among other things, systems, devices, and methods for predicting an occurrence of impending thoracic fluid accumulation and in one example, invoking a responsive therapy, such as to prevent or minimize the consequences of the impending thoracic fluid accumulation. One example of the present systems, devices, and methods senses or receives at least one parameter that is statistically associated with impending thoracic fluid accumulation from a subject. Using such parameter(s), a probability of impending thoracic fluid accumulation is estimated. A list of parameters determines which values are recurrently sensed or received at various desired time intervals. Another example of the present systems, devices, and methods weights the sensed or received parameter value(s) to compute the probability estimate of impending thoracic fluid accumulation. A responsive preventive thoracic fluid accumulation therapy or other therapy is selected and activated using the probability estimate of impending thoracic fluid accumulation.

30 Claims, 7 Drawing Sheets

(56) References Cited

U.S. PATENT DOCUMENTS

| | | | |
|---|---|---|---|
| 5,282,840 A | 2/1994 | Hudrlik et al. | |
| 5,355,894 A | 10/1994 | Sivard | |
| 5,391,190 A | 2/1995 | Pederson et al. | |
| 5,404,877 A | 4/1995 | Nolan et al. | |
| 5,454,377 A | 10/1995 | Dzwonczyk et al. | |
| 5,507,785 A | 4/1996 | Deno | |
| 5,522,860 A | 6/1996 | Molin et al. | |
| 5,562,712 A | 10/1996 | Steinhaus et al. | |
| 5,735,284 A | 4/1998 | Tsoglin et al. | |
| 5,788,643 A | 8/1998 | Feldman | |
| 5,876,353 A | 3/1999 | Riff | |
| 5,957,861 A | 9/1999 | Combs et al. | |
| 6,104,949 A | 8/2000 | Pitts Crick et al. | |
| 6,272,377 B1 | 8/2001 | Sweeney et al. | |
| 6,314,322 B1 | 11/2001 | Rosenberg | |
| 6,336,903 B1 | 1/2002 | Bardy | |
| 6,406,422 B1 * | 6/2002 | Landesberg | 600/17 |
| 6,409,675 B1 * | 6/2002 | Turcott | 600/508 |
| 6,473,640 B1 | 10/2002 | Erlebacher | |
| 6,512,949 B1 | 1/2003 | Combs et al. | |
| 6,595,927 B2 | 7/2003 | Pitts-Crick et al. | |
| 6,600,949 B1 | 7/2003 | Turcott | |
| 6,643,543 B2 | 11/2003 | Takehara et al. | |
| 6,665,564 B2 | 12/2003 | Lincoln et al. | |
| 6,678,547 B2 | 1/2004 | Carlson et al. | |
| 6,714,813 B2 | 3/2004 | Ishigooka et al. | |
| 6,752,765 B1 | 6/2004 | Jensen et al. | |
| 6,811,537 B2 | 11/2004 | Bardy | |
| 6,829,503 B2 | 12/2004 | Alt | |
| 6,908,437 B2 | 6/2005 | Bardy | |
| 6,963,777 B2 | 11/2005 | Lincoln et al. | |
| 2001/0020138 A1 | 9/2001 | Ishigooka et al. | |
| 2002/0026104 A1 | 2/2002 | Bardy | |
| 2002/0123674 A1 | 9/2002 | Plicchi et al. | |
| 2003/0040472 A1 * | 2/2003 | Larsen et al. | 514/12 |
| 2003/0055461 A1 | 3/2003 | Girouard et al. | |
| 2003/0139679 A1 | 7/2003 | Kushnir et al. | |
| 2003/0191503 A1 | 10/2003 | Zhu et al. | |
| 2003/0220580 A1 | 11/2003 | Alt | |
| 2004/0073128 A1 | 4/2004 | Hatlestad et al. | |
| 2004/0102712 A1 | 5/2004 | Belalcazar et al. | |
| 2004/0116819 A1 | 6/2004 | Alt | |
| 2004/0133079 A1 | 7/2004 | Mazar et al. | |
| 2004/0147982 A1 | 7/2004 | Bardy | |
| 2004/0172080 A1 | 9/2004 | Stadler et al. | |
| 2004/0215097 A1 | 10/2004 | Wang | |
| 2004/0215270 A1 | 10/2004 | Ritscher et al. | |
| 2005/0004609 A1 | 1/2005 | Stahmann et al. | |
| 2005/0070778 A1 * | 3/2005 | Lackey et al. | 600/366 |
| 2005/0080460 A1 | 4/2005 | Wang et al. | |
| 2005/0085865 A1 * | 4/2005 | Tehrani | 607/42 |
| 2005/0137480 A1 | 6/2005 | Alt et al. | |
| 2006/0116590 A1 * | 6/2006 | Fayram et al. | 600/508 |
| 2006/0241510 A1 * | 10/2006 | Halperin et al. | 600/534 |

FOREIGN PATENT DOCUMENTS

| | | |
|---|---|---|
| EP | 0663219 A1 | 7/1995 |
| WO | WO-2004050178 A1 | 6/2004 |
| WO | WO-2005018432 A2 | 3/2005 |
| WO | WO-2006127719 A2 | 11/2006 |
| WO | WO-2006127719 A3 | 11/2006 |

OTHER PUBLICATIONS

Adamicza, A., et al., "Changes in transthoracic electrical impedance during endotoxemia in dogs", *Acta Physiol Hung.*, 85(4), (1997-98), 291-302.

Adamicza, A., et al., "Investigation of the thoracic electrical impedance during endotoxemia in dogs", *Acta Chir Hung.*, 36(1-4), (1997), 1-3.

Alt, Eckhard, et al., "Control of Pacemaker Rate by Impedance-based Respiratory Minute Ventilation", *Chest,* 92(2), (Aug. 1987), 247-252.

Baarends, E. M., et al., "Body-water compartments measured by bio-electrical impedance spectroscopy in patients with chronic obstructive pulmonary disease", *Clinical Nutrition,* 17(1), (Feb. 1998), 15-22.

Belalcazar, Andres, et al., "Improved lung edema monitoring with coronary vein pacing leads", *Pacing and Clinical Electrophysiology,* 26(4 pt. II), Abstract 18,(Apr. 2003), 933.

Belalcazar, Andres, et al., "Improved lung edema monitoring with coronary vein pacing leads: a simulation study", *Physiological Measurement,* vol. 25, (2004), 475-487.

Berman, Irwin R., et al., "Transthoracic electrical impedance s a guide to intravascular overload", *Archives of Surgery,* 102(1), (Jan. 1971), 61-64.

Bradbury, M. G., et al., "Assessment of the sensitivity of bioimpedance to volume changes in body water", *Pediatr Nephrol.,* 9(3), (Jun. 1995), 337-40.

Campbell, J. H., et al., "Clinical applications of electrical impedance tomography in the monitoring of changes in intrathoracic fluid volumes", *Physiol. Meas.,* vol. 15, (1994) A217-A222.

Campbell, J. H., et al., "Detection of changes in intrathoracic fluid in man using electrical impedance tomography", *Clinical Science,* vol. 87, (1994), 97-101.

Charach, Gideon , et al., "Transthoracic monitoring of the impedance of the right lung in patients with cardiogenic pulmonary edema", *Critical Care Medicine,* 29(6), (Jun. 2001), 1137-44.

Chiolero, R. L., "Assessment of changes in body water by bioimpedance in acutely ill surgical patients.", *Intensive Care Medicine,* 18(6), (1992), 322-6.

Dargie, H. , et al., "Relation of arrhythmias and electrolyte abnormalities to survival in patients with severe chronic heart failure", *Circulation,* 78(5 *Pt* 2), (May 1987),IV98-107.

Defaye, P., et al., "Automatic Recognition of Abnormal Respiratory Events During Sleep by a Pacemaker Transthoracic Impedance Sensor", *Journal of Cardiovascular Electrophysiology,* 15(9), (Sep. 2004), 1034-40.

Denniston, J. C., et al., "Factors Influencing the measurement of stroke volume by electrical impedance", *Physiology* (1372-1377), Abstract No. 1373, 463.

Denniston, J. C., et al., "Measurement of pleural effusion by electrical impedance.", *Journal of Applied Physiology,* 38(5), (May 1975), 851-7.

Ellenbogen, Kenneth A., et al., "Rate-adaptive pacing based on impedance-derived minute ventilation", *Clinical Cardiac Pacing,* Philadelphia : Saunders, (1995), 219-233.

Ellenbogen, Kenneth A., et al., "The Electrode-Tissue Interface and the Foreign Body Response", *Clinical Cardiac Pacing,* Philadelphia: Saunders, (1995), 22-23.

Fein, Alan, et al., "Evaluation of Transthoracic Electrical Impedance in the Diagnosis of Pulmonary Edema", *Circulation,* 60(5), (Nov. 1979),1156-1160.

Foreman, B., et al., "Intra-thoracic impedance: a surrogate measure of thoracic fluid—fluid accumulation status trial (FAST)", *Journal of Cardiac Failure,* 10(4 *Suppl*), Abstract 251, (2004), S86.

Forro, M., et al., "Total body water and ECFV measured using bioelectrical impedance analysis and indicator dilution in horses", *Journal of Applied Physiology,* 89(2), (Aug. 2000), 663-71.

Frerichs, I., et al., "Electrical impedance tomography in monitoring experimental lung injury", *Intensive Care Med.,* 24(8), (Aug. 1998), 829-36.

Garland, J. S., et al., "Measurement of extravascular lung water in hemodialysis patients using blood ultrasound velocity and optical density dilution.", *ASAIO Journal* 2002 48(4), (Jul.-Aug. 2002), 398-403.

Goovaerts, H. G., et al., "Microprocessor-based system for measurement of electrical impedances during haemodialysis and in postoperative care", *Medical & Biological Engineering & Computing,* vol. 26, (Jan. 1988), 75-80.

Gotshall, R. W., et al., "Bioelectric impedance as an index of thoracic fluid.", *Aviation Space and Environmental Medicine,* 70(1), (Jan. 1999), 58-61.

(56) References Cited

OTHER PUBLICATIONS

Grimbert, F., et al., "Pulmonary water and thoractic impedance. Evaluation of a measurement technic]", *Annales de L'anesthésiologie Française,* 16 Spec. No. 2-3, French,(1975), 157-6.
Harris, N. D., et al., "Applications of applied potential tomography (APT) in respiratory medicine", *Clinical Physics and Physiological Measurements, 8 Suppl A,* (1987), 155-56.
Hoon, Raghunath S., et al., "Changes in Transthoracic electrical impedance at high altitude", *British Heart Journal,* vol. 39, (1977), 61-66.
Hull, E. T., et al., "The Transthoracic Impedance Method for the Determination of the Degree and Change in Extravascular Water", *Acta Tuberc. Pneumol. Belg.,* 68(4), (1977),369-377.
Hull, E. T., et al., "Transthoracic electrical impedance: artifacts associated with electrode movement", *Resuscitation,* 6(2), (1978), 115-124.
Ishibe, Y., et al., "Transthoracic electrical impedance method for measurement of pulmonary edema in vivo", *Masui;* 27(13), Japanese,(Dec. 1978), 1559-67.
Jaski, Brian E., "Basics of Heart Failure: A Problem Solving Approach, Chapter 3, Part 1: The problem of heart failure", *Circulation,* (2000), 42 Pages.
Joekes, A. M., et al., "Impedance Cardiography—Its value in an intensive care unit", *D) Materiels et techniques/Cardiocirculatory Equipment and Technics,* Abstract No. 141, 1 Page.
Keller, Guido, et al., "Monitoring of Pulmonary Fluid Volume and Stroke Volume by Impedance Cardiography in Patients on Hemodialysis", *Chest,* 72(1), (Jul. 1977), 56-62.
Khan, Mahfooz R., et. al., "Quantitive electrical-impedance plethysmography for pulmonary oedema", *Medical & Biological Engineering & Computing,* vol. 15, (Nov. 1977), 627-633.
Kiesler, T. W., et al., "Impedance cardiography by use of a spot-electrode array to track changes in cardiac output in anesthetized dogs.", *Journal of the American Veterinary Medical Association,* 196(11), (Jun. 1, 1990), 1804-10.
Koizumi, T., "Changes of transthoracic impedance (zinf 0 and deltaz) in newborn infants", *Acta Neonatol. Jpn.,* 14(3), (1978), 335-340.
Kunst, P. W., et al., "Electrical impedance tomography in the assessment of extravascular lung water in noncardiogenic acute respiratory failure", *Chest,* 116(6), (Dec. 1999), 1695-702.
Kusumoto, Fred M., et al., "Medical Progress: Cardiac Pacing", *New England Journal of Medicine,* 334(2), (Jan. 11, 1996), 89-98.
Larsen, F., et al., "Influence of furosemide and body posture on transthoracic electrical impedance in AMI", *Chest,* 90(5), (733-7), Nov. 1986.
Lau, C. P., et al., "Rate-responsive pacing with pacemaker that detects respiratory rate (Biorate): clinical advantages and complications", *Clinical Cardiology,* 11(5), (May 1988), 318-24.
Lau, C. P., "The range of sensors and algorithms used in rate adaptive cardiac pacing", *Pacing and clinical electrophysiology: PACE,* 15(8), (Aug. 1992),1177-211.
Leung, Zoe K., et al., "Feasibility of an automatic atrial and ventricular threshold determination using thransthoracic using impedance", *Pacing and Clinical Electrophysiology,* vol. 19, Part II, Abstract 263, (Apr. 1996), 631.
Luepker, R. V., et al., "Transthoracic Electrical Impedance: Quantitive Evaluation of a Non-Invasive Measure of Thoracic Fluid Volume", *American Heart Journal,* 85(1), (Jan. 1973), 83-93.
Mai, J., et al., "Enhanced Rate Response Algorithm for Orthostatic Compensation Pacing", *Pacing Clin Electrophysiol,* 23, Naspe Abstracts, Abstract No. 678, (Apr. 2000), 722.
McCarty, Richard N., et al., "Assessment of pulmonary edema in acute congestive heart failure with impedance cardiography", *J Am Osteopath Assoc.,* 74(9), (May 1975), 879.
McNamee, James E., et al., "Peribronchial electrical admittance measures lung edema and congestion in the dog", *Special Communications, Electrical Admittance and Pulmonary Edema,* 337-341.
Newell, J. C., et al., "Assessment of acute pulmonary edema in dogs by electrical impedance imaging", *IEEE Transactions on Biomedical Engineering,* 43(2), (Feb. 1996), 133-138.
Nierman, D. M., et al., "Evaluation of transthoracic bioelectrical impedance analysis in monitoring lung water during diuresis", *Applied Cardiopulmonary Pathophysiology,* 7(1), (1997), 57-62,
Nierman, David M., "Transthoracic Bioimpedance Can Measure Extravascular Lung Water in Acute Lung Injury1", *Journal of Surgical Research* 65, Article No. 0350, (1996), 101-108.
Noble, T. J., et al., "Diuretic induced change in lung water assessed by electrical impedance tomography", *Physiol Meas.,* 21(1), (Feb. 2000), 155-63.
Nukiwa, Toshihiro, et al., "Responses of Serum and Lung Angiotensin-Converting Enzyme Activities in the Early Phase of Pulmonary Damage Induced by Oleic Acid in Dogs", *Am Rev Respir Dis.,* 126(6), (Dec. 1982), 1080-1086.
Petersen, J. R., et al., "Electrical impedance measured changes in thoracic fluid content during thoracentesis", *Clin Physiol.,* 14(4), (Jul. 1994), 459-66.
Platia, Edward V., et al., "Time Course of Transvenous Pacemaker Stimulation Impedance, Capture Threshold, and Electrogram Amplitude", *Pacing Clin Electrophysiol.,* 9(5), (Sep./Oct. 19), 620-625.
Pomerantz, M., et al., "Transthoracic electrical impedance for the early detection of pulmonary edema", *Surgery,* 66(1), (Jul. 1969), 260-8.
Raaijmakers, E., et al., "Estimation of non-cardiogenic pulmonary oedema using dual-frequency electrical impedance.", *Medical & Biological Engineering & Computing,* 36(4), (Jul. 1998), 461-6.
Ragguenau, J. L., et al., "Monitoring of intracellular and extracellular hydric compartments by body impedance", *Anesth Anal. Rean,* vol. 36, (1979), 439-443.
Ramos, Marcos U., et al., "Transthoracic electric impedance. A clincial guide of pulmonary fluid accumulation in congestive heart failure", *Minnesota Medicine,* 58(9), (Sep. 1975), 671-676.
Rosborough, John P., et al., "Electrical Therapy for Pulseless Electrical Activity", *NASPE,* 23(4), Part II, Abstract,(Apr. 2000),591.
Saunders, Charles E., "The Use of Transthoracic Electrical Bioimpedance in Assessing Thoracic Fluid Status in Emergency Department Patients", *American Journal of Emerienc Medicine,* 6(4), (Jul. 1988),337-340.
Schuster, C. J., et al., "Application of Impedance Cardiography in Critical Care Medicine", *Resuscitation,* vol. 11, (1984), 255-274.
Schwartzman, David, et al., "Serial Defibrillation Lead Impedance in Patients with Epicardial and Nonthoracotomy Lead Systems", *Journal of Cardiovascular Electrophysiology,* 7(8), (Aug. 1996), 697-703.
Shochat, M., et al., "Internal thoracic impedance monitoring: a new prospect in acute heart failure", *European Heart Journal,* 25(Supp), (Aug.-Sep. 2004), p. 72-72.
Shoemaker, William C., et al., "Multicenter trial of a new thoracic electrical bioimpedance device for cardiac output estimation", *Critical Care Medicine,* 22(12), (Dec. 1994), 1907-1912.
Smith, R. M., et al., "Canine thoracic electrical impedance with changes in pulmonary gas and blood volumes.", *Journal of Applied Physiology,* 53(6), (Dec. 1982), 1608-13.
Spinale, F. G., et al., "Noninvasive estimation of extravascular lung water using bioimpedance.", *The Journal of Surgical Research,* 47(6), (Dec. 1989), 535-40.
Stadler, R., et al., "Automated detection of decreases in intrathoracic impedance to predict CHF hospitalization", *Abstract* 263, 26(4 pt II), Abstract 16,(Apr. 2003), 932.
Staub, N. C., "The measurement of lung water content.", *The Journal of Microwave Power* 18(3), (Sep. 1983), 259-63.
Tang, W., "Assessment of total body water using bioelectrical impedance analysis in neonates receiving intensive care", *Arch Dis Child Fetal Neonatal Ed.,* 77(2), (Sep. 1997), F123-6.
Tempel, G., et al., "Transthoracic electrical impendance in anaesthesia and intensive care.", *Resuscitation* 6(2), (1978), 97-105.
Thakur, Ranjan K., et al., "Pericardial Effusion Increases Defibrillation Energy Requirement", *Pacing Clin Electrophysiol.,* 16(6), (Jun. 1993), 1227-1230.

(56) References Cited

OTHER PUBLICATIONS

Vainshtein, G. B., et al., "The Functioning of the Cerebral Circulation Sytem in Hyperthermia in Rabbits", *Fiziol Zh SSSR Im I M Sechenova,* 75(11), (Nov. 1989), 1608-1614.
Van De Water, Joseph M., et al., "Monitoring the Chest with Impedance", *Chest,* 64(5), (Nov. 1973), 597-603.
Viirola, H., "Controlled growth of antimony-doped tin dioxide thin films by atomic layer epitaxy", *Thin Solid Films,* 251, (Nov. 1994),127-135.
Viirola, H., et al., "Controlled growth of tin dioxide thin films by atomic layer epitaxy", *Thin Solid Films,* 249(2), (Sep. 1994), 144-149.
Visokay, M. R., "Application of HfSiON as a gate dielectric material", *Applied Physics Letters,* 80(17), (Apr. 2002), 3183-3185.
Wang, L., et al., "Impedance based prediction of CHF admission precedes symptoms in heart failure patients", *Heartrhythm : the official journal of the Heart Rhythm Society,* 1(Suppl 1), Abstract 679,(2004), S213.
Wang, Li, et al., "Multiple Sources of the Impedance Cardiogram Based on 3-D Finite Difference Human Thorax Models", *IEEE Transactions on Biomedical Engineering,* 42(2), (Feb. 1995), 141-148.
Wang, L., et al., "Prediction of CHF hospitalization by ambulatory intrathoracic impedance measurement in CHF patients is feasible using pacemaker or ICD lead systems", *Pacing and Clinical Electrophysiology,* 26(4 pt. II), Abstract 123,(Apr. 2003), 959.
Wuerz, Richard C. et al., "Effects of prehospital medications on mortality and length of stay in congestive heart failure", *Annals of Emergency Medicine,* 21(6), (Jun. 1992), 669-74.
Yu, C., et al., "Changes in device based thoracic impedance in decompensating congestive heart failure", *Circulation,* 104(17 supplement), Abstract 1994,(2001), II-419.
Yu, C. M., et al., "Correlation of device-based intra-thoracic impedance and patient fluid status during intravenous diuretic therapy in acute CHF", *European Heart Journal,* 23(Abstract Supplement), (2002), 158.
Yu, C., et al., "Device-based intra-thoracic impedance correlates with fluid status and provides automaticed prediction of CHF hospitalization", *Journal of Cardiac Failure,* 10(4 Suppl), Abstract 354,(2004), S113.
Yu, C., et al., "Early warning of CHF hospitalization by intra-thoracic impedance measurement in CHF patients with pacemakers", *Pacing and Clinical Electrophysiology: PACE,* 24(4 pt II), Abstract 19,(2002), 527.
Yu, Cheuk-Man, et al., "Early warning of CHF hospitalization by intra-thoracic impedance measurement in CHF patients with pacemakers", *Pacing and Clinical Electrophysiology,* 24, (Apr. 2001),19.
Yu, C. M., et al., "Impedance measurements from implanted devices provide automated prediction of CHF hospitalization", *European Heart Journal,* 25(Suppl), (Aug.-Sep. 2004), p. 27-27.
Yu, C. M., et al., "Intrathoracic impedance: A surrogate measure of fluid retention and predictor of hospitalization in patients with heart failure", *Journal of the American College of Cardiology,* 41(6 Supplement A), Abstract 1206-70,(2003), 210A.
Zellner, J. L., et al., "Bioimpedance: a novel method for the determination of extravascular lung water.", *The Journal of Surgical Research* 48(5), (May 1990), 454-9.
Zima, E., "Intracardiac impedance in biventricular electrode configuration for left ventricular volume monitoring", *European Heart Journal,* 25(Suppl), (Aug.-Sep. 2004), p. 165-165.
"Japanese Application No. 2008-513627, Office Action mailed Aug. 31, 2011", 6 pgs.
"Japanese Application No. 2008-513627, Response filed Feb. 29, 2012 to Office Action mailed Aug. 31, 2011", With English Claims, 7 pgs.

* cited by examiner

PREDICTION OF THORACIC FLUID ACCUMULATION

TECHNICAL FIELD

This patent document pertains generally to medical systems, devices, and methods, and more particularly, but not by way of limitation, to medical systems, devices, and methods associated with thoracic fluid accumulation.

BACKGROUND

Congestive heart failure (CHF), which is also sometimes referred to simply as "heart failure," is a condition in which a subject's heart can't pump the needed amount of blood to the subject's other organs. Heart failure may result from a variety of causes, some of which include: a narrowing of arteries that supply blood to the heart muscle (coronary artery disease); a past heart attack or myocardial infarction, with scar tissue that interferes with the heart muscle's normal work; a high blood pressure condition; a heart valve disease due to past rheumatic fever or other causes; a primary disease of the heart muscle itself (cardiomyopathy); a heart defect present at birth (congenital heart defects); or an infection of the heart valves or heart muscle itself (endocarditis or myocarditis).

Heart failure can be conceptualized as an enlarged weakened heart muscle, which results in poor cardiac output of blood. As blood flow out of the heart slows, blood returning to the heart through the veins backs up, causing congestion in bodily tissues. This congestion may cause swelling in the legs, ankles, or other parts of the body and may also result in fluid collecting in the subject's thorax, which may become a barrier to normal oxygen exchange.

The fluid build-up in the thorax may result in pulmonary edema or pleural effusion. These conditions, if left untreated, may in turn lead to death. Pulmonary edema includes the build-up of extravascular fluid in the lungs. During pulmonary edema, fluid accumulates in extracellular spaces, such as the spaces between lung tissue cells. Pleural effusion, on the other hand, is the build-up of extravascular fluid in the space between the lungs and the rib cage. The lungs are covered by a membrane called the pleura, which has two layers, an inner layer and an outer layer. The outer layer lines the rib cage and diaphragm. The inner layer covers the lungs. The pleura produces a fluid, which acts as a lubricant to help in breathing, allowing the lungs to move in and out smoothly. Pleural effusion is the accumulation of too much of such fluid. Both pulmonary edema and pleural effusion, if they exist, present medical emergencies that require immediate (oftentimes challenging) care and can sometimes prove fatal.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in this document.

DETAILED DESCRIPTION

Figure 1:
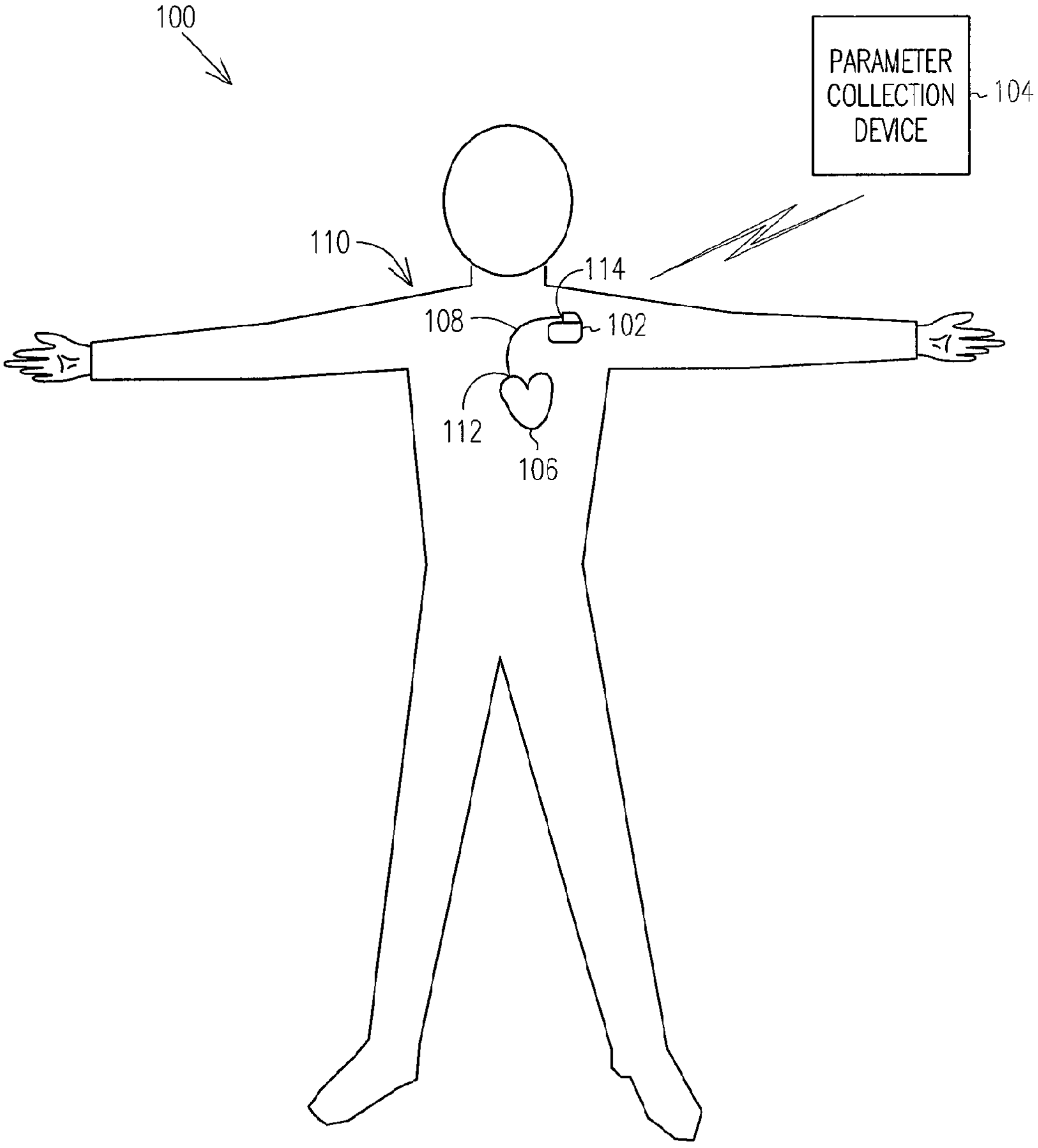
FIG. 1 is a schematic view illustrating generally, one example of portions of a system adapted to predict an occurrence of impending thoracic fluid accumulation in a subject, and an environment in which the system is used.

The following detailed description includes references to the accompanying drawings, which form a part of this detailed description. The drawings show, by way of illustration, specific embodiments in which the present systems, devices, and methods may be practiced. These embodiments, which are also referred to herein as "examples," are described in enough detail to enable those skilled in the art to practice the present systems, devices, and methods. The embodiments may be combined, other embodiments may be utilized, or structural, logical or electrical changes may be made without departing from the scope of the present systems, devices, and methods. It is also to be understood that the various embodiments of the present systems, devices, and methods, although different, are not necessarily mutually exclusive. For example, a particular feature, structure or characteristic described in one embodiment may be included with other embodiments. The following detailed description is, therefore, not to be taken in a limiting sense, and the scope of the present systems, devices, and method are defined by the appended claims and their legal equivalents.

In this document: the terms "a" or "an" are used to include one or more than one; the term "or" is used to refer to a nonexclusive or, unless otherwise indicated; the term "thorax" is used to refer to a human subject's body between the neck and diaphragm; the term "subject" is used to include the term "patient"; the term "prediction" is used to denote a probability assertion or statement regarding whether or not an occurrence of impending thoracic fluid accumulation will occur during a specified prediction time period; and the term "user" includes a caregiver, a subject, a loved one or others who may ascertain or provide a parameter statistically associated with impending thoracic fluid accumulation to the present systems, devices, and methods.

Furthermore, all patents and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Introduction

Today, heart failure is a major cause of hospital admissions and expenditures in the United States. It is estimated that heart failure contributes to more than 4 million hospitalizations per year, which cost upwards of 12 billion dollars. Many of these hospital admissions are due to thoracic fluid accumulation in subjects, which may result in pulmonary edema or pleural effusion. As discussed above, both pulmonary edema and pleural effusion may be challenging to treat and may result in critical illness. Unfortunately, the time associated with detection of thoracic fluid accumulation may be too late to prevent the significant clinical intervention (e.g., hospitalization) resulting from such fluid accumulation.

The present systems, devices, and methods predict an occurrence of impending thoracic fluid accumulation in subjects and further, in one example, adjust or initiate one or more therapies to prevent, decrease, or minimize such impending fluid accumulation using the prediction. As will be discussed below, the prediction of impending thoracic fluid accumulation is made, in part, by sensing or receiving conditions (e.g., physiologic parameters, therapeutic parameters, or environmental parameters) that cause or predispose a subject to thoracic fluid accumulation and by comparing such conditions to thoracic fluid accumulation prediction criteria. Advantageously, prediction of impending thoracic fluid accumulation may reduce or eliminate the intervention needed (e.g., hospitalization) and be useful for avoiding decompensation crises and properly managing a heart failure subject in a state of relative well-being.

EXAMPLES

The present systems, devices, and methods provide techniques for predicting and preventing the occurrence of impending thoracic fluid accumulation, and such techniques can be used in applications involving implantable medical devices (IMDs) including, but not limited to, implantable cardiac rhythm management (CRM) systems such as pacemakers, cardioverter/defibrillators, pacer/defibrillators, biventricular or other multi-site resynchronization or coordination devices such as cardiac resynchronization therapy (CRT) devices, patient monitoring systems, and drug delivery systems. However, the systems, devices, and methods described herein may also be employed in unimplanted devices, including but not limited to, external pacemakers, cardioverter/defibrillators, pacer/defibrillators, biventricular or other multi-site resynchronization or coordination devices, monitors, programmers and recorders, whether such devices are used for providing detection, differentiation, or therapy.

FIG. 1 is a schematic view illustrating generally, one example of portions of a system 100 adapted to predict an occurrence of impending thoracic fluid accumulation in a subject 110, and an environment in which the system 100 may be used. In FIG. 1, system 100 includes an implantable medical device (IMD) 102, such as a cardiac rhythm management (CRM) device, which is coupled by one or more leadwires 108 to a heart 106 of subject 110. IMD 102 may be implanted subcutaneously in the subject's chest or elsewhere. The one or more leadwires 108 each include a proximal end 114, which is coupled to IMD 102, and a distal end 112, which is coupled to one or more portions of heart 106. System 100 also includes a parameter collection device 104, a portion of which is shown in FIG. 1. In this example, parameter collection device 104 provides wireless communication with IMD 102 using telemetry. In another example, prediction of the occurrence of impending fluid accumulation is made, at least in part, by sensing or receiving at least one thoracic fluid accumulation parameter (e.g., a parameter that is statistically associated with impending thoracic fluid accumulation) via parameter collection device 104. In another example, parameter collection device 104 includes a visual or other display for relaying information to a user regarding operation of system 100, such as IMD 102.

Figure 2:
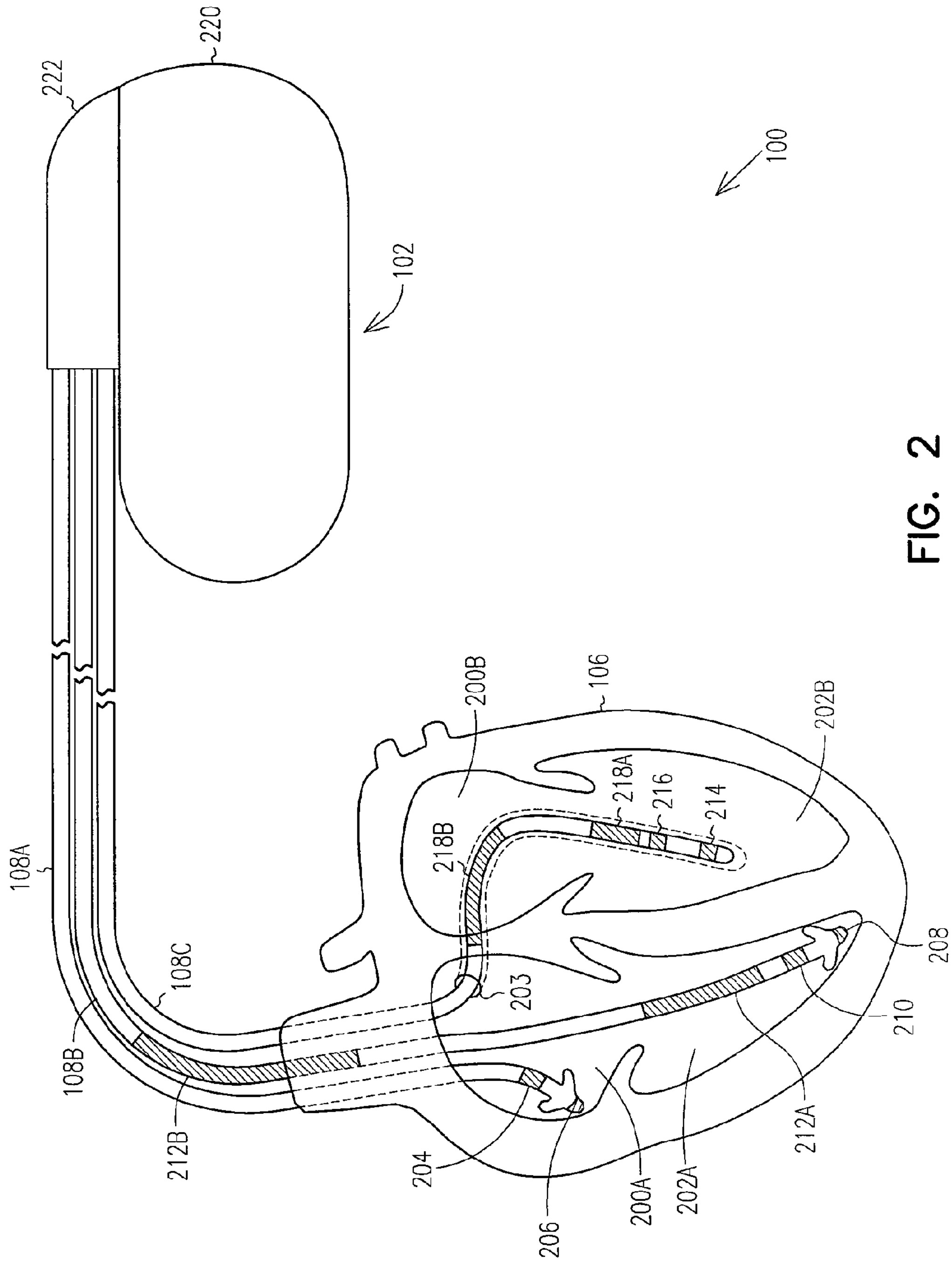
FIG. 2 is a schematic view illustrating generally, one example of an implantable medical device of a system, the implantable medical device is coupled by a plurality of leads to a heart.

FIG. 2 is a schematic view illustrating generally, one example of an IMD 102 of a system 100, the IMD 102 is coupled by a plurality of leads 108A-108C to a heart 106, which includes a right atrium 200A, a left atrium 200B, a right ventricle 202A, a left ventricle 202B, and a coronary sinus 203 extending from right atrium 200A. In this example, atrial lead 108A includes electrodes (e.g., electrical contacts) disposed in, around, or near right atrium 200A of heart 106, such as ring electrode 204 and tip electrode 206, for sensing signals (e.g., via sensing module 302 (FIG. 3A)) or delivering pacing therapy (e.g., via therapy module 304 (FIG. 3A)) to right atrium 200A. Lead 108A may also include additional electrodes, such as for delivering atrial or ventricular cardioversion/defibrillation or pacing therapy to heart 106.

In FIG. 2, a right ventricular lead 108B includes one or more electrodes, such as tip electrode 208 and ring electrode 210, for sensing signals (e.g., via sensing module 302) or delivering pacing therapy (e.g., via therapy module 304). Lead 108B may also include additional electrodes, such as coil electrodes 212A or 212B for delivering right atrial or right ventricular cardioversion/defibrillation or pacing therapy to heart 106. In one example, system 100 also includes a left ventricular lead 108C, which provides one or more electrodes such as tip electrode 214 and ring electrode 216, for sensing signals (e.g., via sensing module 302) or delivering pacing therapy (e.g., via therapy module 304). Lead 108C may also include one or more additional electrodes, such as coil electrodes 218A or 218B for delivering left atrial or left ventricular cardioversion/defibrillation or pacing therapy to heart 106.

In FIG. 2, IMD 102 includes components that are enclosed in a hermetically-sealed enclosure, such as a can 220. Additional electrodes may be located on the can 220, or on an insulating header 222, or on other portions of IMD 102, such as for sensing or for providing pacing or defibrillation energy, for example, in conjunction with the electrodes disposed on or around heart 106. Other forms of electrodes include meshes and patches which may be applied to portions of heart 106 or which may be implanted in other areas of the body to help direct electrical currents produced by IMD 102. For example, an electrode on insulating header 222 may be used to stimulate local muscle to provide an alert/warning to a subject 110. The present systems, devices, and methods are adapted to work in a variety of electrode configurations and with a variety of electrical contacts or electrodes.

Figure 3A:
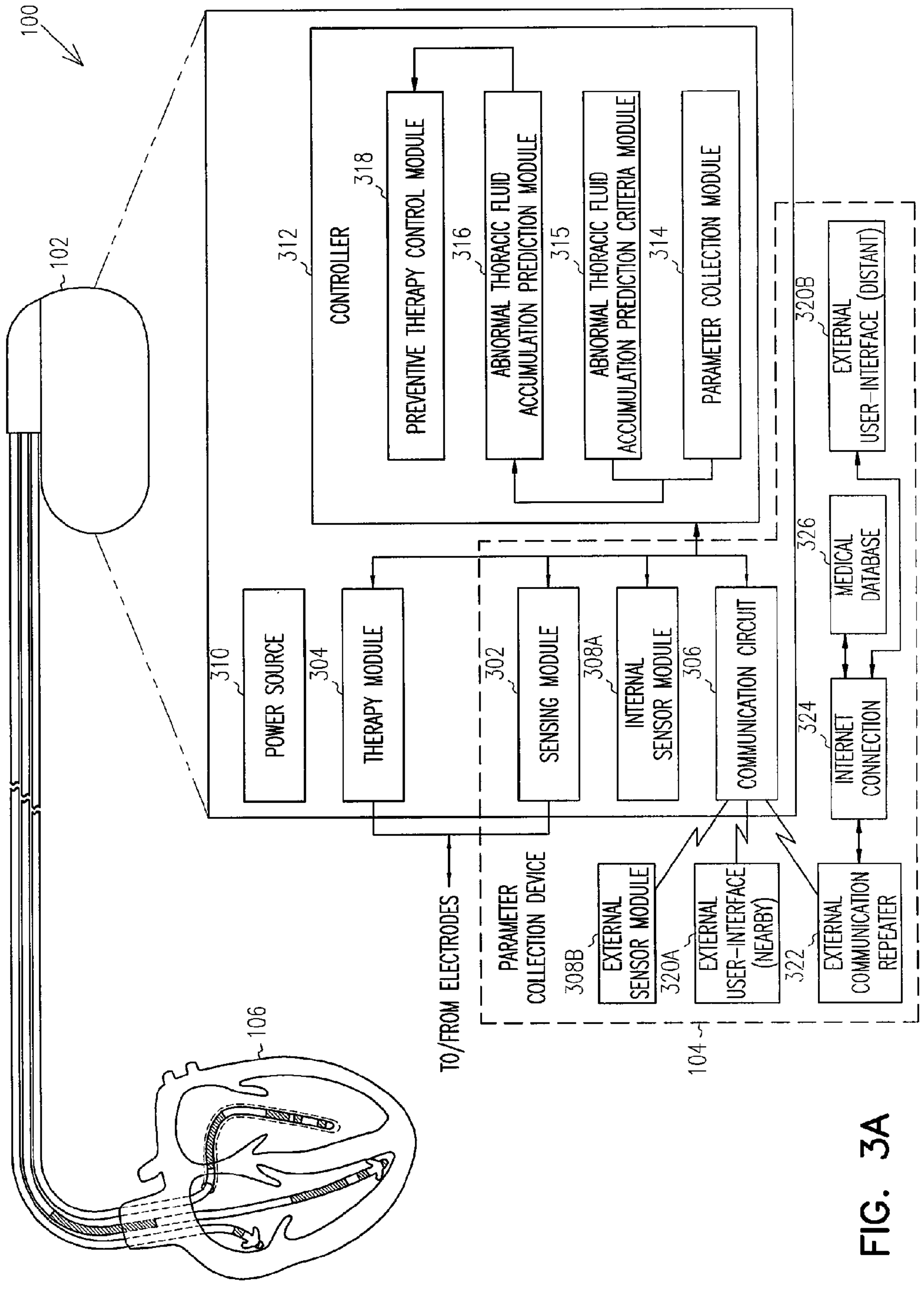
FIG. 3A is a schematic diagram illustrating generally, one conceptual example of portions of a system adapted to predict an occurrence of impending thoracic fluid accumulation in a subject, the system is coupled to a heart or other portions of the subject's body.

FIG. 3A is a schematic diagram illustrating generally, one example of portions of a system 100 adapted to predict an occurrence of impending thoracic fluid accumulation in a subject 110. The system 100 is coupled to a heart 106 or other portions of the subject's body 110. FIG. 3A illustrates one conceptualization of various modules and devices, which are implemented either in hardware or as one or more sequences of steps carried out on a microprocessor or other controller. Such modules and devices are illustrated separately for conceptual clarity; however, it is to be understood that the various modules and devices of FIG. 3A need not be separately embodied, but may be combined or otherwise implemented, such as in software or firmware. IMD 102 may be powered by a power source 310, such as a battery.

In FIG. 3A, system 100 includes, among other things, a parameter collection device 104 adapted to sense or receive at least one thoracic fluid accumulation parameter. The at least one thoracic fluid accumulation parameter is output to a controller 312 for performing the prediction of the occurrence of impending thoracic fluid accumulation. In one example, the at least one thoracic fluid accumulation parameter is a physiologic parameter corresponding to detection of a physiologic state that is statistically associated with impending thoracic fluid accumulation. In another example, the at least one thoracic fluid accumulation parameter is a therapeutic parameter corresponding to detection of a therapeutic state that is statistically associated with impending thoracic fluid accumulation. In a further example, the at least one thoracic fluid accumulation parameter is an environmental parameter corresponding to detection of an environmental state that is statistically associated with impending thoracic fluid accumulation.

In FIG. 3A, parameter collection device 104 includes: a sensing module 302, an internal sensor module 308A, a communication module 306, an external sensor module 308B, an external user interface 320A (which is typically nearby), an external communication repeater 322, an Internet or other communication network connection 324, a computerized medical database 326, and an external user interface 320B (which is typically distant). Sensing module 302, internal sensor module 308A, and communication module 306 are coupled to controller 312. External sensor module 308B, (nearby) external user interface 320A, and external communication repeater 322 are communicatively coupled with communication module 306 via telemetry. In this example, communication module 306 is capable of wirelessly communicating with computerized medical database 326 or (distant) external user interface 320B, such as by using external communication repeater 322 and Internet connection 324. In one example, external user interface 320A or 320B controls, loads and retrieves information from IMD 102, and is adapted to process and display such information obtained.

The sensing module 302 senses intrinsic heart activity signals from one or more electrodes associated with heart 106. These intrinsic heart activity signals typically include depolarizations that propagate through heart tissue. The depolarizations cause heart contractions for pumping blood through the circulatory system. Controller 312 may include sense amplifier circuits or other signal processing circuits to extract depolarizations or other useful information from the intrinsic heart activity signals.

In FIG. 3A, internal or external sensor modules 308A or 308B include, among other things, one or more sensors, such as an accelerometer, acoustic sensor (e.g., microphone), posture sensor, impedance or other respiration or stroke volume sensor, breathing rate sensor, pressure sensor, echocardiogram or other imaging instrument, transdermal sensor, drug level detector, or cardiac dimension sensor (e.g., sensor using ultrasonic transit time measurements). In one example, sensor module 308A or 308B also includes one or more interface circuits that receive one or more control signals and preprocesses the sensor signal(s) received. System 100 also includes a control circuit, such as a microprocessor or other controller 312, which communicates with the various peripheral circuits. In FIG. 3A, IMD 102 includes controller 312; however, in one example (as discussed above), external user interface 320A or 320B controls, loads and retrieves information from IMD 102, and is adapted to process and display such information obtained (e.g., includes a control circuit). In another example, information collected from IMD 102 is otherwise externally (from IMD 102) processed. Controller 312 includes various functional modules, one conceptualization of which is illustrated in FIG. 3A.

In one example, controller 312 includes a parameter collection module 314 that receives from the parameter collection device 104 the at least one thoracic fluid accumulation parameter. Parameter collection module 314 may include a memory to store such thoracic fluid accumulation parameters and may further classify such thoracic fluid accumulation parameters as one or more of: a physiologic parameter, a therapeutic parameter, or an environmental parameter. In this example, controller 312 also includes a prediction criteria module 315 adapted to store one or more thoracic fluid accumulation prediction criteria. In one example, the one or more thoracic fluid accumulation prediction criteria is derived using one or more past observation of an occurrence of thoracic fluid accumulation (e.g., signs, symptoms, or other parameters relating thereto and stored in computer medical database 326) in the subject 110 from whom the at least one thoracic fluid accumulation parameter is sensed or received. In another example, the one or more thoracic fluid accumulation prediction criteria is derived using one or more past observation of an occurrence of thoracic fluid accumulation (e.g., signs, symptoms, or other parameters relating thereto and stored in computer medical database 326) in at least one subject other than the subject 110 from whom the at least one thoracic fluid accumulation parameter is sensed or received. In a further example, the one or more thoracic fluid accumulation prediction criteria is loaded into IMD 102 before, during, or after (e.g., entered into external user interface 320A or 320B) IMD 102 is implanted in the subject 110.

For predicting and preventing the occurrence of impending thoracic fluid accumulation, controller 312 includes a thoracic fluid accumulation prediction module 316 and a therapy control module 318. Thoracic fluid accumulation prediction module 316 is coupled to prediction criteria module 315 to receive the one or more thoracic fluid accumulation prediction criteria, and is coupled to parameter collection module 314 to receive the at least one thoracic fluid accumulation parameter. Thoracic fluid accumulation prediction module 316 predicts the likelihood of future impending thoracic fluid accumulation using the one or more thoracic fluid accumulation prediction criteria and the thoracic fluid accumulation parameter information. Therapy control module 318 selects from a set of available therapies the most appropriate responsive therapy (or combination of therapies), such as for reducing the likelihood or even preventing the predicted occurrence of impending thoracic fluid accumulation. In one example, therapy control module 318 also triggers the delivery of such therapy after determining if the probability of the occurrence of impending thoracic fluid accumulation, computed by thoracic fluid accumulation prediction module 316, and the expected outcome of the selected therapy warrants administration of the therapy by a therapy module 304.

Therapy module 304 provides therapy, such as for treating present thoracic fluid accumulation and preventing impeding thoracic fluid accumulation. In one example, such therapy is provided at electrodes associated with heart 106 or portions of a subject's nervous system such as, for example, sympathetic or parasympathetic members of the autonomic nervous system. In various other examples, such electrode-associated therapy includes pacing pulses, antitachyarrhythmia pacing (ATP), defibrillation shocks, cardiac resynchronization therapy (CRT), etc. In another example, such therapy is provided elsewhere (e.g., to the subject's nasal system or communicated to external user interface 320A or 320B) and includes a continuous positive air pressure (CPAP) dose, a recommended drug dose, a diet regimen, or a fluid intake regimen.

Figure 3B:
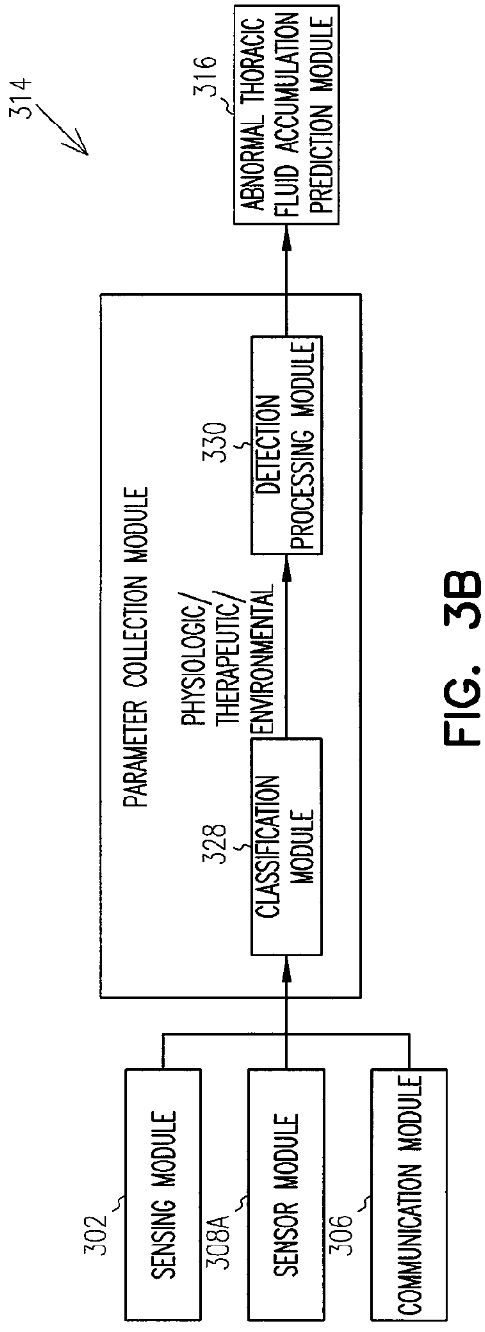
FIG. 3B is a block diagram illustrating generally, one conceptual example of a portion of a parameter collection module.

FIG. 3B is a block diagram illustrating generally, one conceptual example of a portion of parameter collection module 314. In one example, parameter collection module 314 includes a classification module 328 and a detection processing module 330. Parameter collection module 314 recurrently receives, stores, and examines (e.g., classifies or detects the presence, time, or magnitude of) signals (corresponding to the thoracic fluid accumulation parameters) from sensing module 302, sensor module 308A, or communication module 306. Classification module 328 separates the received thoracic fluid accumulation parameter signals into one or more categories including: physiologic parameters, therapeutic parameters, or environments parameters. The classified thoracic fluid accumulation parameter signals are then output to detection processing module 330 which detects the presence, time, or magnitude of the signals. From the parameter collection device 314, the thoracic fluid accumulation parameter signals are output to thoracic fluid accumulation prediction module 316.

Figure 3C:
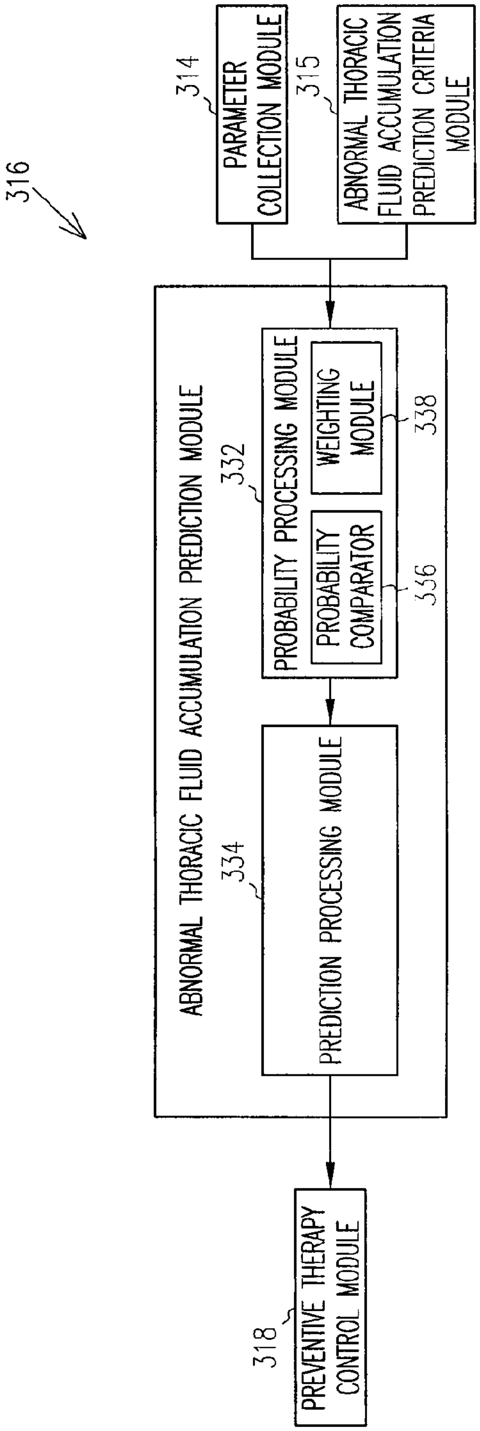
FIG. 3C is a block diagram illustrating generally, one conceptual example of a portion of a thoracic fluid accumulation prediction module.

FIG. 3C is a block diagram illustrating generally one conceptual example of a portion of thoracic fluid accumulation prediction module 316. In one example, thoracic fluid accumulation prediction module 316 includes a probability processing module 332 and a prediction processing module 334. In another example, thoracic fluid accumulation prediction module 316 includes an input that receives the thoracic fluid accumulation parameter signals ($S_1, S_2, \ldots, S_N$) from the parameter collection module 314. In a further example, thoracic fluid accumulation prediction module 316 includes an input that receives the one or more thoracic fluid accumulation prediction criteria from prediction criteria module 315.

In one example, probability processing module 332 includes a weighting module 338 and a probability comparator 336. After entering thoracic fluid accumulation prediction module 316, the thoracic fluid accumulation parameter signals ($S_1, S_2, \ldots, S_N$) and the thoracic fluid accumulation prediction criteria are received by probability processing module 332. Probability comparator 336 compares each thoracic fluid accumulation parameter signal ($S_1, S_2, \ldots, S_N$) value to a corresponding thoracic fluid accumulation prediction criteria ($C_1, C_2, \ldots, C_N$) value. For each parameter signal ($S_1, S_2, \ldots, S_N$) value exceeding or substantially similar to the corresponding prediction criteria ($C_1, C_2, \ldots, C_N$) value, probability comparator 336 summarizes and outputs to prediction processing module 334 a probability indication of the occurrence of impending thoracic fluid accumulation.

In another example, weighting module 338 stores weighting factors ($Weight_1, Weight_2, \ldots, Weight_N$), wherein each weighting factor corresponds to a different one of the thoracic fluid accumulation parameter signals received by probability processing module 332. Weighting factors may be used for computing the probability indication of the occurrence of impending thoracic fluid accumulation (e.g., provide a degree to which each thoracic fluid accumulation parameter signal value exceeding or substantially similar to the corresponding thoracic fluid accumulation prediction criteria value enters into the probability indication). In general, each weight ($Weight_1, Weight_2, \ldots, Weight_N$) is computed using historical data relating the corresponding sensed or received thoracic fluid accumulation parameter (e.g., physiologic parameter, therapeutic parameter, or environment parameter) to the occurrence of impending thoracic fluid accumulation. In one example, the historical data is obtained from the same subject 110 from whom the thoracic fluid accumulation parameter information is obtained (e.g., by accessing data in computerized medical database 326). In another example, the historical data is obtained from at least one different subject from whom the thoracic fluid accumulation parameter information is obtained (e.g., by accessing data in computerized medical database 326). In a further example, the historical data is obtained from a population of subjects.

In another example, a weight is computed using not only its corresponding thoracic fluid accumulation parameter, but also using information about which other thoracic fluid accumulation parameter (or how many other thoracic fluid accumulation parameters) are also being used to predict the occurrence of impending thoracic fluid accumulation. As an illustrative example, suppose thoracic fluid accumulation parameters A and B each have weights of 0.1, leading to a combined prediction weight of 0.2. In another example, however, thoracic fluid accumulation parameters A and B each have weights of 0.1 when these parameters are individually used in the occurrence of impending thoracic fluid accumulation prediction, but have a different (e.g., greater or lesser) weight when both are present (e.g., stronger weights of 0.5 when both A and B are sufficiently present and used in the occurrence of impending thoracic fluid accumulation prediction). In sum, the weight values may depend on cross-correlation between two or more different thoracic fluid accumulation parameters. In a further example, a weight value depends on how many thoracic fluid accumulation parameters are being used to compute the predicted occurrence of impending thoracic fluid accumulation. As an illustrative example, suppose thoracic fluid accumulation parameter A has a weight of 0.5 when it is used alone for predicting the occurrence of impending thoracic fluid accumulation. In another example, however, thoracic fluid accumulation parameter A has a weight of 0.25 when used in combination with one other different thoracic fluid accumulation parameter (e.g., thoracic fluid accumulation parameter B or thoracic fluid accumulation parameter C, etc.).

In one example, prediction processing module 334 generates, using the probability indication output from probability processing module 332, a probability assertion or statement that an occurrence of impending thoracic fluid accumulation will occur during a specified period after the prediction. An example of such a probability assertion or statement is a 50% probability that an occurrence of impending thoracic fluid accumulation will occur during 5 days of the prediction generation. This assertion or statement of prediction includes both a magnitude (e.g., 50%) and a well defined time period during which the prediction is applicable (e.g., 5 days).

Thoracic fluid accumulation prediction module 316 outputs an impending thoracic fluid accumulation prediction to therapy control module 318, which in turn bases delivery of preventive therapy or other therapy on the impending thoracic fluid accumulation prediction. In one example, as discussed above, the impending thoracic fluid accumulation prediction output from thoracic fluid accumulation prediction module 316, such as the prediction processing module 334, includes a set of one or more probability assertions or statements. Each probability statement includes both a magnitude of the probability (e.g., 50% probability of impending thoracic fluid accumulation exists) and a specified future time period associated therewith. In another example, each probability statement also identifies which thoracic fluid accumulation parameter signal(s) (sensed or received by parameter collection device 104) contributed to its magnitude. In a further example, the time period covered by each probability statement (e.g., the time period over which each probability statement is valid) is determined by, among other things, the scheduled prediction frequency (e.g., predictions made at N minute intervals covers a N minute period, etc.).

In an alternative example, the impending thoracic fluid accumulation prediction calculation and output from thoracic fluid accumulation prediction module 316 takes the form of a conditional probability computation, such as described in Sweeney et al., U.S. Pat. No. 6,272,377 entitled, "CARDIAC RHYTHM MANAGEMENT SYSTEM WITH ARRHYTHMIA PREDICTION AND PREVENTION," and Girouard et al., U.S. Patent Application Serial No. 2003/0055461 entitled, "CARDIAC RHYTHM MANAGEMENT SYSTEMS AND METHODS PREDICTING CONGESTIVE HEART FAILURE STATUS," each of which are assigned to Cardiac Pacemakers, Inc., and the disclosures of which are incorporated herein by reference in their entirety, including their descriptions of using condition probabilities to predict the likelihood of occurrence of a future event. In the present context, the future event is thoracic fluid accumulation, and the thoracic fluid accumulation parameters (physiologic parameters, therapeutic parameters, or environmental parameters) sensed or received serve as triggers/markers or, more generally, conditioning events. The weights correlating each thoracic fluid accumulation parameter (signal) to a future thoracic fluid accumulation are conditional probabilities that may alternatively be expressed as rates, as described in the above-incorporated Sweeney et al. reference.

Figure 3D:
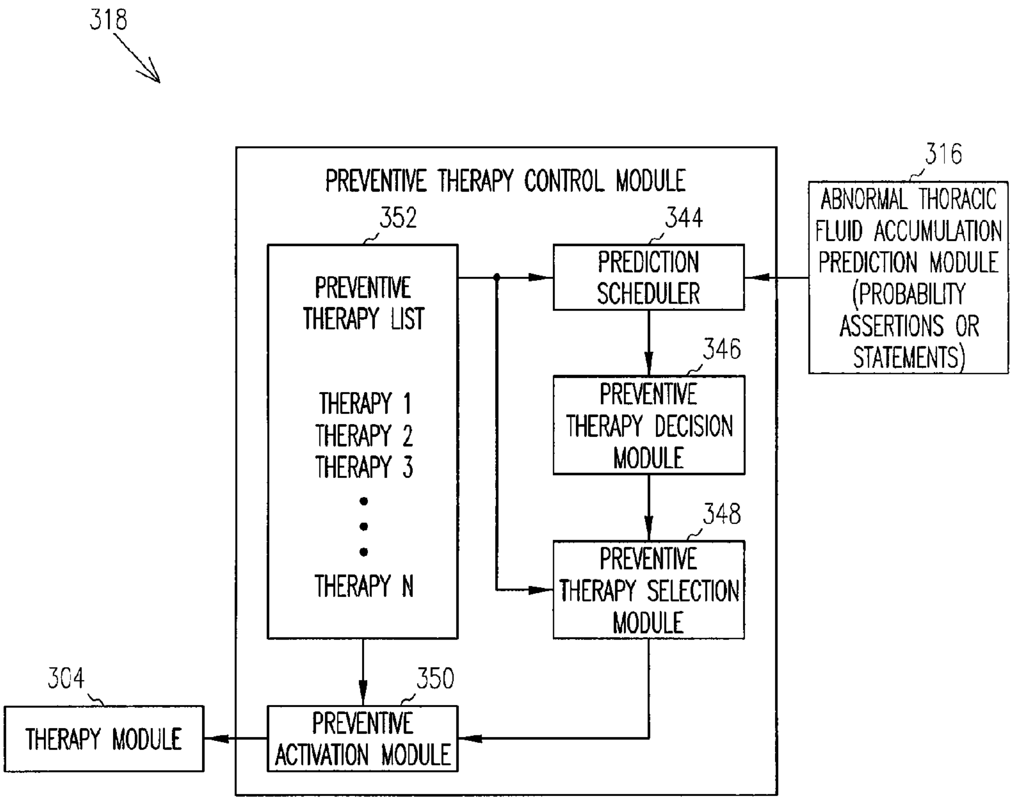
FIG. 3D is a block diagram illustrating generally, one conceptual example of a portion of a therapy control module.

FIG. 3D is a block diagram illustrating generally, one conceptual example of a portion of a therapy control module 318. In one example, therapy control module 318 includes an input that receives the probability assertions or statements output from thoracic fluid accumulation prediction module 316. In this example, prediction scheduler 344 schedules predictions of impending thoracic fluid accumulation. Therapy decision module 346 decides whether therapy is warranted. Therapy selection module 348 selects one or more appropriate therapies. Activation module 350 activates the selected therapy via an output to therapy module 304. Therapy control module 318 also includes a therapy list 352, which may include means to relate the therapies of therapy list 352 to the thoracic fluid accumulation parameter(s) (sensed or received by parameter collection device 104) used by thoracic fluid accumulation prediction module 316 in predicting the occurrence of impending thoracic fluid accumulation. The various submodules in therapy control module 318 are illustrated as such for conceptual purposes only; however, these submodules may alternatively be incorporated in thoracic fluid accumulation prediction module 316 or elsewhere.

In one example, therapy selection module 348 selects a thoracic fluid accumulation prevention therapy using outputs from therapy decision module 346. If therapy decision module 346 determines that the degree and confidence in the impending thoracic fluid accumulation prediction warrants some therapy, then therapy selection module 348 selects a member of the therapy list 352 to be invoked. In another example, therapy section module 348 selects a therapy (e.g., CRT) that is only secondarily related to thoracic fluid accumulation.

In one example, therapy list 352 includes all possible thoracic fluid accumulation preventive therapies or secondarily related therapies that system 100 may deliver or communicate to the subject 110. List 352 may be programmed into IMD 102 either in hardware, firmware, or software. In another example, therapy list 352 includes immediate, short-term, intermediate-term, or long-term thoracic fluid accumulation preventive therapies.

Immediate thoracic fluid accumulation preventive therapies include, by way of example, initiating or changing a drug therapy (e.g., diuretics) administered to a subject 110 via an implantable drug pump.

Short-term thoracic fluid accumulation preventive therapies include, by way of example, administering continuous positive air pressure (CPAP) dose to subject 110 or notifying caregiver to initiate or change subject's drug treatment program (e.g., increase diuretic dose).

Intermediate-term thoracic fluid accumulation preventive therapies include, by way of example, adjusting subject's 110 lifestyle (e.g., decrease salt or water consumption).

Long-term thoracic fluid accumulation preventive therapies include, by way of example, notifying caregiver or subject 110 to alter the drug which takes longer to affect the subject (e.g., beta blockers, ACE inhibitors) or administering CRT to the subject.

According to one example of the present system 100, each member of therapy list 352 is associated with a required time of action, which includes one or more of a time for the therapy to become effective or a time after which the therapy is no longer effective. Accordingly, in one example, the prediction scheduler 344 considers only those members of the therapy list that can be expected to be effective within a time frame commensurate with the prediction time period. In another example, only one member of the therapy list 352 is invoked at any particular time. In a further example, combinations of different therapies are provided.

Figure 4:
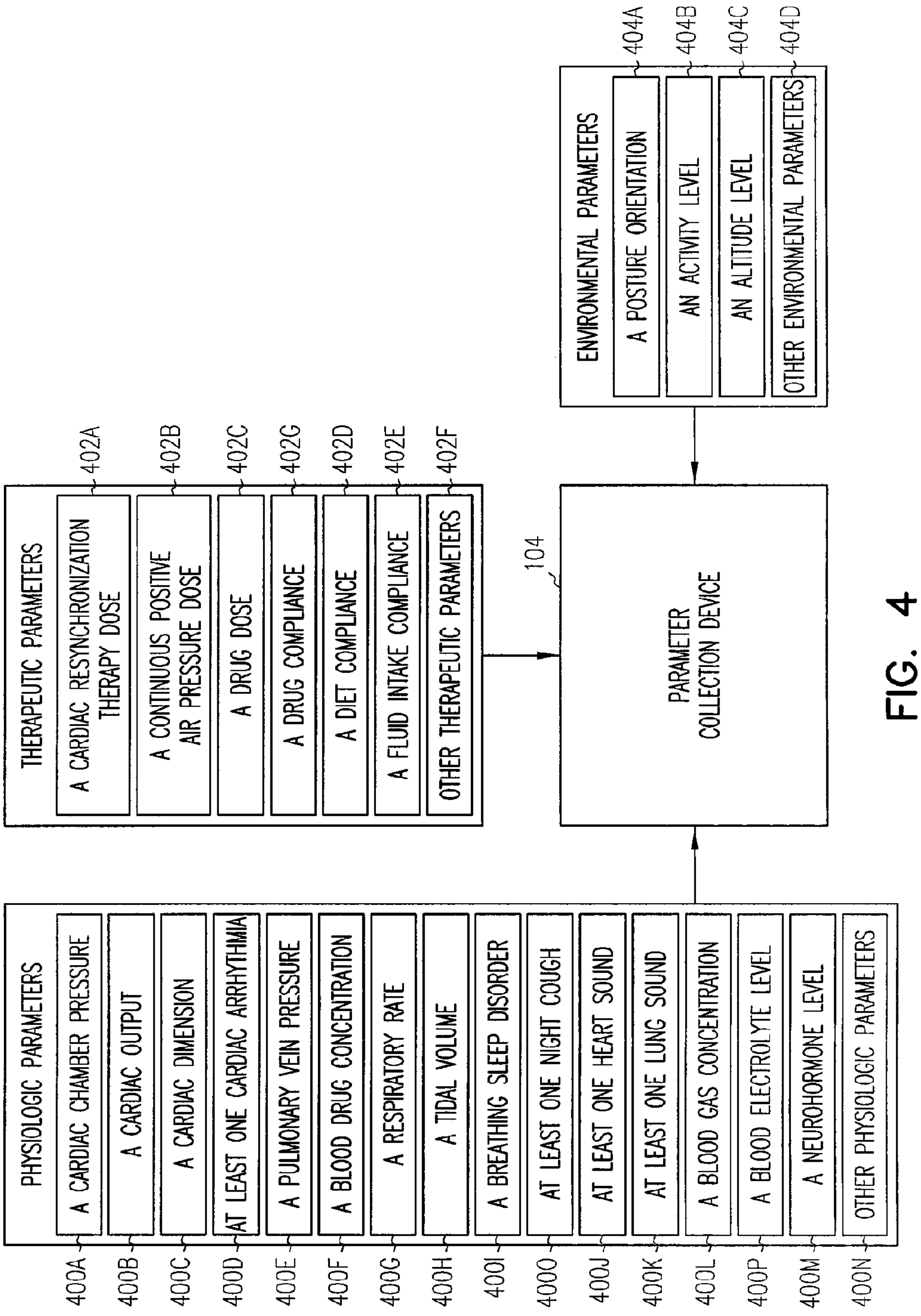
FIG. 4 is a block diagram illustrating generally, parameters which may be used to predict an occurrence of impending thoracic fluid accumulation in a subject.

FIG. 4 is a block diagram illustrating generally, parameters statistically associated with an occurrence of impending thoracic fluid accumulation. In one example, one or more physiologic parameter 400A-P, therapeutic parameter 402A-G, or environmental parameter 404A-D are used, in part, to predict an occurrence of impending thoracic fluid accumulation (in a subject 110). In another example, the one or more physiologic parameter 400A-P, therapeutic parameter 402A-G, or environmental parameter 404A-D are used, in part, to predict an occurrence of impending thoracic fluid accumulation (in a subject 110) within a specified prediction time period. In this example, the one or more physiologic parameter 400A-P, therapeutic parameter 402A-G, or environmental parameter 404A-D used to predict the occurrence of impending thoracic fluid accumulation within the specified prediction time period is sensed (from the subject 110) or received (from a user) by way of parameter collection device 104.

In one example, the subject's left ventricular end diastolic pressure (LVEDP) is used as a physiologic parameter 400A that is statistically associated with impending thoracic fluid accumulation. In one example, LVEDP is measured using internal sensor module 308A (e.g., implantable pressure sensor disposed within the subject's left ventricle). An increase in LVEDP may correlate to a future thoracic fluid accumulation.

In another example, the subject's left atrial pressure (LA pressure) is used as a physiologic parameter 400A that is statistically associated with impending thoracic fluid accumulation. In one example, LA pressure is measured using internal sensor module 308A (e.g., implantable pressure sensor disposed within the subject's left atrium). An increase in LA pressure may correlate to a future thoracic fluid accumulation.

In another example, the subject's cardiac output is used as a physiologic parameter 400B that is statistically associated with impending thoracic fluid accumulation. In one example, the subject's cardiac output is measured noninvasively (e.g., external sensor module 308B) via impedance cardiography (ICG). Cardiac output is the volume of blood ejected from the heart in one minute. A decrease in cardiac output may correlate to a future thoracic fluid accumulation.

In another example, the subject's cariomegaly (e.g., enlargement of the heart) is used as a physiologic parameter 400C that is statistically associated with impending thoracic fluid accumulation. In one example, the subject's heart size is measured by sensing module 302 (e.g., implantable transthoracic impedance sensing circuit). As an example, a reduced cardiac stroke component of a transthoracic impedance signal correlates to an increase in heart size. In another example, the subject 110, caregiver, or other user enters an indication of the subject's heart size found using an echocardiogram or other imaging instrument, into external user interface 320A or 320B. An increase in heart size may correlate to a future thoracic fluid accumulation.

In another example, a cardiac arrhythmia experienced by the subject 110 is used as a physiologic parameter 400D that is statistically associated with impending thoracic fluid accumulation. In one example, the at least one cardiac arrhythmia is measured by sensing module 302, which is coupled to a plurality of electrodes associated with the subject's heart. In another example, the subject 110, caregiver, or other user enters a detected presence of the cardiac arrhythmia, using an echocardiogram or other imaging instrument, into external user interface 320A or 320B. A cardiac arrhythmia is any disorder of heart rate or rhythm. The presence of one or more cardiac arrhythmias may correlate to a future thoracic fluid accumulation.

In another example, the subject's pulmonary vein pressure is used as a physiologic parameter 400E that is statistically associated with impending thoracic fluid accumulation. In one example, the subject's pulmonary vein pressure is measured by internal sensor module 308A (e.g., a pulmonary vein or right ventricular pressure transducer). In another example, the subject 110, caregiver, or other user enters an indication of the subject's pulmonary vein pressure (e.g., based on an external measurement) into external user interface 320A or 320B. An increase in pulmonary vein pressure may correlate to a future thoracic fluid accumulation.

In another example, the subject's blood drug concentration is used as a physiologic parameter 400F that is statistically associated with impending thoracic fluid accumulation. In one example, the subject's blood drug concentration is measured directly by internal sensor module 308A (e.g., implantable drug level detector). In another example, the subject's blood drug concentration is determined by internal sensor module 308A (e.g., implantable respiratory sensor which senses a biological signal indicative of blood drug concentration). In yet another example, the subject's blood drug concentration is determined in response to the subject 110 inputting to external user interface 320A or 320B an indication of what drug(s) he/she has consumed. A low blood drug concentration may correlate to a future thoracic fluid accumulation.

In another example, the subject's respiratory rate is used as a physiologic parameter 400G that is statistically associated with impending thoracic fluid accumulation. In one example, the subject's respiratory rate is measured by internal sensor module 308A (e.g., implantable breathing rate module which includes a fiducial point detector detecting a fiducial point on the breathing signal that occurs a known number of one or more times during breathing cycle and a timer measuring the time interval between respective successive fiducial points). An increased respiratory rate pattern may correlate to a future thoracic fluid accumulation.

In another example, the subject's tidal volume is used as a physiologic parameter 400H that is statistically associated with impending thoracic fluid accumulation. In one example, the subject's tidal volume is measured by sensing module 302 (e.g., an impedance signal obtained between two intracardiac electrodes). A decrease in tidal volume may correlate to a future thoracic fluid accumulation.

In another example, the subject's shortness of breath while sleeping (e.g., paroxysmal nocturnal dyspnea or orthopnea) is used as a physiologic parameter 400I that is statistically associated with impending thoracic fluid accumulation. In one example, paroxysmal nocturnal dyspnea or orthopnea is measured by internal sensor module 308A (e.g., a respiratory impedance sensor) to detect the shortness of breath and a sleep detector. One example of a sleep detector is described in Carlson et al., U.S. patent application Ser. No. 09/802,316, entitled "CARDIAC RHYTHM MANAGEMENT SYSTEM USING TIME-DOMAIN HEART RATE VARIABILITY INDICIA," which is assigned to Cardiac Pacemakers, Inc., and which is incorporated herein by reference in its entirety, including its description of a sleep detector. Another example of a sleep detector is described in Hatlestad et al., U.S. Patent Application Serial No. 2004/0073128, entitled "DETECTION OF CONGESTION FROM MONITORING PATIENT RESPONSE TO RECUMBENT POSITION," which is assigned to Cardiac Pacemakers, Inc., and which is incorporated herein by reference in its entirety, including its description of a sleep detector. In another example, the subject 110, caregiver, or other user enters an indication of the degree of paroxysmal nocturnal dyspnea or orthopnea into external user interface 320A or 320B. An increase in paroxysmal nocturnal dyspnea or orthopnea may correlate to a future thoracic fluid accumulation.

In another example, the subject's Cheyne-stokes respiration is used as a physiologic parameter 400I that is statistically associated with impending thoracic fluid accumulation. In one example, the Cheyne-stokes respiration is measured by internal sensor module 308A and a clock, a sleep detector, or a posture detector. Cheyne-stokes respiration is a breathing pattern characterized by rhythmic oscillation of tidal volume with regularly recurring periods of hyperpnoea, hypopnoea and apnoea. An increase in Cheyne-stokes respiration may correlate to a future thoracic fluid accumulation.

In another example, the subject's night cough is used as a physiologic parameter 4000 that is statistically associated with impending thoracic fluid accumulation. In one example, the night cough is measured by internal sensor module 308A (e.g., a transthoracic impedance sensor) to detect the cough and a clock, a sleep detector, or a posture detector to respectively detect a time during the night, the subject's sleep, or the subject's lying down. In another example, the subject 110, caregiver, or other user enters an indication of the subject's night cough into external user interface 320A or 320B. An increase in night cough may correlate to a future thoracic fluid accumulation.

In another example, the subject's heart sounds (for example, heart sounds referred to in the art as $S_1$, $S_2$, and particularly the heart sound referred to in the art as $S_3$) are used as a physiologic parameter 400J that is statistically associated with impending thoracic fluid accumulation. In one example, the heart sounds are measured by internal sensor module 308A (e.g., an implantable accelerometer, microphone, or other implantable sensor), such as by using the systems and methods described in Lincoln et al., U.S. Pat. No. 6,665,564, entitled "CARDIAC RHYTHM MANAGEMENT SYSTEM SELECTING A-V DELAY BASED ON INTERVAL BETWEEN ATRIAL DEPOLARIZATION AND MITRAL VALVE CLOSURE," or other systems and methods described in Lincoln et al., U.S. patent application Ser. No. 10/099,865, entitled "CARDAIC RHYTHM MANAGEMENT SYSTEM AND METHOD USING TIME BETWEEN MITRAL VALVE CLOSURE AND AORTIC EJECTION," each of which is assigned to Cardiac Pacemakers, Inc., and the disclosures of which are incorporated herein by reference in their entirety, including their description of heart sound detection. In another example, the heart sounds are measured by a caregiver while the subject 110 is lying on his/her left side, and a numerical value indicative of a heart sound frequency or amplitude is input to external user interface 320A or 320B by the caregiver, subject 110, or other user. An increase in certain heart sound frequency or amplitude, such as $S_3$ frequency or amplitude, may correlate to a future thoracic fluid accumulation.

In another example, the subject's changed pulmonary (lung) sounds (e.g., increased rales) is used as a physiologic parameter 400K that is statistically associated with impending thoracic fluid accumulation. In one example, the changed pulmonary sounds are measured by internal sensor module 308A (e.g., an implantable accelerometer, microphone, or other implantable sensor). In another example, the subject 110, caregiver, or other user enters an indication of the degree of increased frequency or amplitude of the rales into external user interface 320A or 320B. An increase in the frequency or amplitude of rales may correlate to a future thoracic fluid accumulation.

In another example, the subject's blood gas concentration is used as a physiologic parameter 400L that is statistically associated with impending thoracic fluid accumulation. In one example, the blood gas concentration (e.g., partial pressure of oxygen ($PaO_2$); partial pressure of carbon dioxide ($PaCO_2$); pH; bicarbonate ($HCO_3$); oxygen content ($O_2CT$); or oxygen saturation ($O_2Sat$)) value is measured externally by a caregiver and entered into external user interface 320A or 320B. One example of a blood gas concentration test is an arterial blood gas (ABG) test which measures the level of both oxygen and carbon dioxide in the blood to determine how well the subject's lungs are working. The ABG test evaluates the subject's lungs ability to move oxygen into the blood and to remove carbon dioxide from the blood. Such test may be performed by drawing blood from an artery, where the oxygen and carbon dioxide levels can be measured before they enter body tissues and become changed. A decrease in $PaO_2$, $PaCO_2$, pH, $O_2CT$, or $O_2Sat$ may correlate to a future thoracic fluid accumulation.

In another example, the subject's blood electrolyte level is used as a physiologic parameter 400P that is statistically associated with impending thoracic fluid accumulation. An electrolyte is a substance that can conduct electrical current; in the human body, magnesium, potassium, calcium, and sodium are electrolytes. In one example, the subject 110 or other user inputs to external user interface 320A or 320B an indication of the subject's serum sodium level. In another example, the subject's serum sodium level is measured by internal sensor module 308A (e.g., implantable sensor) or external sensor module 308B (e.g., transdermal sensor). A low serum sodium concentration (e.g., less than 130) indicates high neurohormonal activation associated with high arginine vasopressin and angiotension II levels and may correlate to a future thoracic fluid accumulation. In another example, the subject 110 or other user inputs to external user interface 320A or 320B an indication of the subject's serum potassium level. In another example, the subject's serum potassium level is measured by internal sensor module 308A (e.g., implantable sensor) or external sensor module 308B (e.g., transdermal sensor). Serum level of potassium should be maintained between 4.0 and 4.8 mEq/dL. Both too-little and too-much potassium can cause heart arrhythmias; therefore, a serum level of potassium less than 4.0 mEq/dL or greater than 4.8 mEq/dL may correlate to a future thoracic fluid accumulation. In yet another example, the subject 110 or other user inputs to external user interface 320A or 320B an indication of the subject's serum magnesium level. In still another example, the subject's serum magnesium level is measured by internal sensor module 308A (e.g., implantable sensor) or external sensor module 308B (e.g., transdermal sensor). Almost all chemical reactions in the body require an enzyme system to take place. Magnesium is a co-factor in more than 300 enzyme reactions in the human body (e.g., potassium without magnesium will not enter cells) and should be maintained at a level greater than 1.8 mEq/dL. Therefore, a serum level below 1.8 mEq/dL may correlate to a future thoracic fluid accumulation.

In another example, the subject's neurohormone level (particularly the neurohormone level referred to in the art as brain, or B-type, natriaetic peptide (BNP)) is used as a physiologic parameter 400M that is statistically associated with impending thoracic fluid accumulation. In one example, the subject's BNP level is measured by an external blood test, and an indication of the BNP level is input to parameter collection device 104 by a user at external user interface 320A or 320B. In another example, the subject's BNP is measured by internal sensor module 308A (e.g., implantable sensor) or external sensor module 308B (e.g., transdermal sensor). BNP is a chemical released by the subject's body in response to left ventricular stress (e.g., volume expansion or pressure overload). An increase in BNP may correlate to a future thoracic fluid accumulation during the specified time period. In another example, atrial natriaetic peptide (ANP), a measure of atrial stress, may also be useful in predicting future thoracic fluid accumulation.

In another example, the cardiac resynchronization therapy (CRT) parameter (e.g., dose amount) experienced by the subject 110 is used as a therapeutic parameter 402A that is statistically associated with impending thoracic fluid accumulation. In one example, the CRT dose amount is sensed and performed by sensing module 302. CRT typically coordinates the spatial nature of a depolarization associated with a heart contraction in one or more heart chambers for improving pumping efficiency. Some examples of CRT include simultaneous or offset multichamber (e.g., biventricular) pacing or simultaneous or offset delivery of pacing pulses to multiple electrodes associated with a single heart chamber. A decrease in the CRT dose amount experienced by the subject 110 may correlate to a future thoracic fluid accumulation.

In another example, the continuous positive air pressure (CPAP) parameter (e.g., dose amount) experienced by the subject 110 is used as a therapeutic parameter 402B that is statistically associated with impending thoracic fluid accumulation. In one example, the subject 110, caregiver, or other user inputs to external user interface 320A or 320B a CPAP dose amount experienced by the subject 110 in a specified period of time. One example of CPAP is nasal CPAP, which uses a blower pump to generate continuous positive air pressure and a nasal mask to apply it to the airways of the subject 110. A decrease in CPAP dose amount experienced by the subject 110 may correlate to a future thoracic fluid accumulation.

In another example, the drug dose parameter (e.g., amount consumed by the subject 110) is used as a therapeutic parameter 402C that is statistically associated with impending thoracic fluid accumulation. In one example, the subject 110 or other user inputs to external user interface 320A or 320B a drug dose amount consumed by the subject 110. Example of drug types include: angiotension-converting enzyme (ACE) inhibitors, beta blockers, digitalis, diuretics, vasodilators, and the like. ACE inhibitors and vasodilators expand blood vessels and decrease resistance. This allows blood to flow more easily and makes the subject's heart work easier or more efficient. Beta blockers can improve how well the subject's heart's left lower chamber (left ventricle) pumps. Digitalis increase the pumping action of the subject's heart, while diuretics help the subject's body eliminate excess salt and water. A decrease in drug dose amount consumed by the subject 110 may correlate to a future thoracic fluid accumulation.

In another example, the subject's drug compliance parameter is used as a therapeutic parameter 402G that is statistically associated with impending thoracic fluid accumulation. In one example, the subject 110 or other user inputs to external user interface 320A or 320B an indication of the subject's compliance to a drug regimen. To determine the indication, a caregiver may call the subject 110 daily or every other day to ask him/her whether he/she has taken all of the medication prescribed. Alternative or additionally, the caregiver may organize a week's worth of medication for the subject 110 in a "pill" box and direct the subject to return at week's end to receive the following week's medication. When the subject 110 returns, the caregiver may take note of whether or not the subject consumed all of his/her prescribed medication based on the amount of pills remaining in the box. A subject's non-compliance with the drug regimen may correlate to a future thoracic fluid accumulation.

In another example, the subject's diet compliance parameter is used as a therapeutic parameter 402D that is statistically associated with impending thoracic fluid accumulation. In one example, the subject 110 or other user inputs to external user interface 320A or 320B an indication of the subject's compliance to a dietary regimen. As an example, the dietary regimen may include, among other things, restriction of sodium to 2 grams or less per day and no more than one alcoholic drink per day. A subject's non-compliance with the dietary regimen may correlate to a future thoracic fluid accumulation.

In another example, the subject's fluid intake compliance parameter is used as a therapeutic parameter 402E that is statistically associated with impending thoracic fluid accumulation. In one example, the subject 110 or other user inputs to external user interface 320A or 320B an indication of the subject's compliance to a fluid intake regimen. As an example, the fluid intake regimen may include advisement to avoid excessive fluid intake. A subject's non-compliance with the fluid intake regimen (e.g., consumption of excessive fluids) may correlate to a future thoracic fluid accumulation.

In another example, the subject's posture orientation is used as an environmental parameter 404A that is statistically associated with impending thoracic fluid accumulation. In one example, the subject's posture orientation is sensed by internal sensor module 308A (e.g., an implantable posture sensor or accelerometer). One example of a suitable posture sensor commercially available is a two-axis accelerometer, such as Model No. ADXL202E, manufactured by Analog Devices, Inc. of Norwood, Mass., U.S.A.; however, other posture sensors may also be used without departing from the scope of the present systems, devices, and methods. Posture changes may affect an amount of fluid the subject 110 has in his/her thorax. For example, moving from a supine position to a standing position can shift intravascular fluid away from the subject's thorax toward the subject's lower extremities thereby decreasing the amount of thoracic fluid present. A subject's 110 increasingly supine posture orientation may correlate to a future thoracic fluid accumulation.

In another example, the subject's 110 activity level is used as an environmental parameter 404B that is statistically associated with impending thoracic fluid accumulation. In one example, the subject's activity level is sensed by internal sensor module 308A (e.g., an implantable accelerometer). In another example, an indication of the subject's activity level is input to external user interface 320A or 320B by the subject 110 or other user. The subject's activity level may correlate to how the subject is feeling (e.g., whether the subject is experiencing a shortness of breath) at a given time. Accordingly, a decrease in the subject's activity level may correlate to a future thoracic fluid accumulation.

In one example, an altitude level of the subject 110 is used as an environmental parameter 404C that is statistically associated with impending thoracic fluid accumulation. In one example, the altitude level of the subject is measured externally (e.g., via an air pressure sensor) and input to external user interface 320A or 320B by the subject, or other user. An increase an altitude is associated with a decrease in environmental oxygen level. As a result, an increase in altitude may correlate to a future thoracic fluid accumulation.

The above discussed physiologic, therapeutic, and environment parameters statistically associated with an occurrence of impending thoracic fluid accumulation are not meant to be exhaustive, and may include other physiologic 400N, therapeutic 402F, or environmental 404D parameters not herein discussed.

Figure 5:
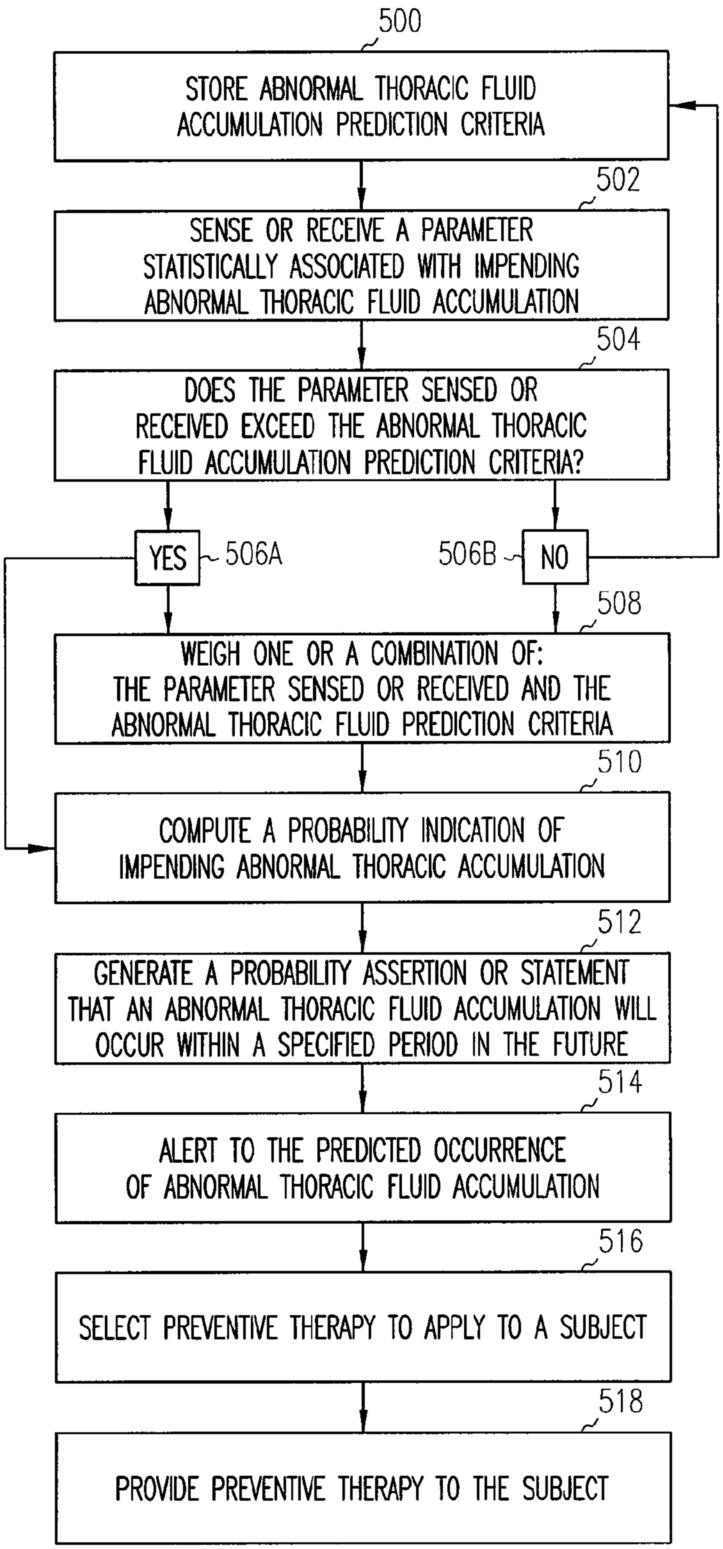
FIG. 5 is a flow chart illustrating generally, one example of a method of predicting an occurrence of impending thoracic fluid accumulation in a subject.

FIG. 5 is a flow chart illustrating generally, one example of a method of predicting an occurrence of impending thoracic fluid accumulation in a subject 110. At 500, one or more thoracic fluid accumulation prediction criteria are stored. This may be accomplished in a number of ways. In one example, the one or more thoracic fluid accumulation prediction criteria are loaded into IMD 102 before, during, or after (e.g., entered into external user interface 320A or 320B) IMD 102 is implanted in the subject 110. The one or more thoracic fluid accumulation prediction criteria may be established in a number of ways. In one example, the one or more thoracic fluid accumulation prediction criteria are derived using one or more past observation of an occurrence of thoracic fluid accumulation in the subject 110 from whom the at least one thoracic fluid accumulation parameter is sensed or received. In another example, the one or more thoracic fluid accumulation prediction criteria are derived using one or more past observation of an occurrence of thoracic fluid accumulation in at least one subject other than the subject 110 from whom the at least one thoracic fluid accumulation parameter is sensed or received.

At 502, at least one thoracic fluid accumulation parameter statistically associated with impending thoracic fluid accumulation is sensed or received. This may be accomplished in a number of ways. In one example, the at least one thoracic fluid accumulation parameter is sensed or received via parameter collection device 104. The at least one thoracic fluid accumulation parameter may be of various types. In one example, the at least one thoracic fluid accumulation parameter is a physiologic parameter corresponding to detection of a physiologic state statistically associated with impending thoracic fluid accumulation. In one such example, the at least one physiologic parameter is selected from a physiologic group consisting essentially of: a cardiac chamber pressure, a cardiac output, a cardiac dimension, at least one cardiac arrhythmia, a pulmonary vein pressure, a blood drug concentration, a respiratory rate, a tidal volume, a breathing sleep disorder, at least one night cough, at least one heart sound, at least one lung sound, a blood gas concentration, a blood electrolyte level, and a neurohormone level. In another example, the at least one thoracic fluid accumulation parameter is a therapeutic parameter corresponding to detection of a therapeutic state statistically associated with impending thoracic fluid accumulation. In one such example, the therapeutic parameter is selected from a therapeutic group consisting essentially of: a cardiac resynchronization therapy parameter, a continuous positive air pressure parameter, a drug dose parameter, a drug compliance parameter, a diet compliance parameter, and a fluid intake compliance parameter. In a further example, the at least one parameter is an environmental parameter corresponding to detection of an environmental state statistically associated with impending thoracic fluid accumulation. In one such example, the environmental parameter is selected from an environmental group consisting essentially of: a posture orientation, a subject activity level, and an altitude level.

At 504, the at least one thoracic fluid accumulation parameter sensed or received is compared with the one or more thoracic fluid accumulation prediction criteria. This may be accomplished in a number of ways. In one example, a probability comparator 336, of thoracic fluid accumulation prediction module 316, compares each thoracic fluid accumulation parameter signal ($S_1, S_2, \ldots, S_N$) value to corresponding thoracic fluid accumulation prediction criteria ($C_1, C_2, \ldots, C_N$) value. When the value of the thoracic fluid accumulation parameter (signal) sensed or received does not exceed and is not substantially similar to the value of the thoracic fluid accumulation prediction criteria, a negative probability indication of the occurrence of impending thoracic fluid accumulation results at 506(*b*) and the process returns to 500. When the value of the thoracic fluid accumulation parameter (signal) sensed or received does exceed or is substantially similar to the value of the thoracic fluid accumulation prediction criteria, a positive probability indication of the occurrence of impending thoracic fluid accumulation results at 506(*a*).

At 508, each thoracic fluid accumulation parameter signal ($S_1, S_2, \ldots, S_N$) value exceeding or substantially similar to the corresponding thoracic fluid accumulation prediction criteria ($C_1, C_2, \ldots, C_N$) value is weighed. This may be accomplished in a number of ways. In one example, for each thoracic fluid accumulation parameter signal ($S_1, S_2, \ldots, S_N$) value exceeding or substantially similar to the corresponding thoracic fluid accumulation prediction criteria ($C_1, C_2, \ldots, C_N$) value, weighting module 338 of thoracic fluid accumulation prediction module 316 stores weighting factors ($Weight_1, Weight_2, \ldots, Weight_N$). In another example, each weighting factor ($Weight_1, Weight_2, \ldots, Weight_N$) provides a degree to which each thoracic fluid accumulation parameter signal exceeding or substantially similar to the corresponding thoracic fluid accumulation prediction criteria enters into a probability indication computed at 510. In yet another example, each weight is computed using not only its corresponding thoracic fluid accumulation parameter, but also using information about which other thoracic fluid accumulation parameter (or how many other thoracic fluid accumulation parameters) are also being used to predict the occurrence of impending thoracic fluid accumulation.

At 512, a probability assertion or statement of impending thoracic fluid accumulation is made. This may be accomplished in a number of ways. In one example, prediction processing module 334 of thoracic fluid accumulation module 316 generates, using the probability indication output, a probability assertion or statement that a thoracic fluid accumulation will occur (e.g., within a specified time period after the prediction). In another example, at least one of the sensing or receiving, comparing, or predicting is performed, at least in part, implantably.

At 514, an alert of the predicted occurrence of impending thoracic fluid accumulation is provided to the subject 110, a caregiver, or a loved one. The alert may be communicated in a number of ways. In one example, an audible tone is sounded. In another example, the subject 110 is linked up to a remote monitoring system (e.g., via repeater 322) thereby allowing the alert to be electronically communicated to the caregiver for review. In a further example, the alert includes transmitting information about the predicted occurrence of impending thoracic fluid accumulation to an external user interface 320A or 320B.

At 516, one or more appropriate therapies are selected. In one example, one or more responsive preventive thoracic fluid accumulation therapy is selected. In another example, one or more therapy secondarily related to thoracic fluid accumulation is selected. Therapy selection may be accomplished in a number of ways. In one example, a therapy selection module 348 selects the one or more appropriate preventive or other therapies. At 518, a therapy is adjusted or initiated using the predicted occurrence of impending thoracic fluid accumulation (e.g., within a specified prediction time period). This may be accomplished in a number of ways. In one example, activation module 350 activates the selected therapy via an output to therapy module 304.

CONCLUSION

Heart failure is a common clinical entity, particularly among the elderly, but is often not treated (if at all) until the disease is detected via associated symptoms such as (abnormal) thoracic fluid accumulation. Advantageously, the present systems, devices, and methods allow for prediction of impending thoracic fluid accumulation. The time savings provided by prediction (as opposed to detection alone), may reduce or eliminate expensive hospitalization and aid in avoiding decompensation crises or properly managing a heart failure subject in a state of relative well-being. Further, the present systems, devices, and methods provide an alert to a user regarding the prediction of impending thoracic fluid accumulation. Further yet, the present systems, devices, and methods may adjust (or initiate) a therapy to prevent or minimize impending fluid accumulation using the prediction.

As discussed above, this Detailed Description is not to be taken in a limiting sense, and the scope of various embodiments is defined only by the appended claims, along with the full range of legal equivalents to which such claims are entitled. In the appended claims, the term "including" is used as the plain-English equivalent of the term "comprising." Also, in the following claims, the terms "including" and "comprising" are open-ended, that is, a system, device, article, or process that includes elements in addition to those listed after such a term in a claim are still deemed to fall within the scope of that claim.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system comprising:

a prediction criteria module, adapted to store one or more thoracic fluid accumulation prediction criteria;

a parameter collection device, adapted to sense or receive at least one thoracic fluid accumulation parameter that is statistically associated with impending thoracic fluid accumulation; and a thoracic fluid accumulation prediction module, coupled to the prediction criteria module to receive the one or more thoracic fluid accumulation prediction criteria, and coupled to the parameter collection device to receive the at least one thoracic fluid accumulation parameter, wherein the thoracic fluid accumulation prediction module includes a probability processing module and a prediction processing module, the probability processing module for comparing the one or more thoracic fluid accumulation prediction criteria and the at least one thoracic fluid accumulation parameter and outputting to the prediction processing module a probability indication of the occurrence of impending thoracic fluid accumulation; and wherein the prediction processing module generates, using the probability indication output from the probability processing module, a probability assertion that an occurrence of impending thoracic fluid accumulation will occur during a specified time after the prediction, wherein the probability assertion includes both a magnitude of the probability assertion and a defined time period during which the prediction is applicable, and wherein the probability assertion identifies which of the at least one thoracic fluid accumulation parameters contributed to the magnitude of the probability assertion.

2. The system of claim 1, wherein the at least one thoracic fluid accumulation parameter is a physiologic parameter that is selected from a physiologic group consisting essentially of a cardiac chamber pressure, a cardiac output, a cardiac dimension, at least one cardiac arrhythmia, a pulmonary vein pressure, a blood drug concentration, a respiratory rate, a tidal volume, a breathing sleep disorder, at least one night cough, at least one heart sound, at least one lung sound, a blood gas concentration, a blood electrolyte level, and a neurohormone level.

3. The system of claim 1, wherein the at least one thoracic fluid accumulation parameter is a therapeutic parameter that is selected from a therapeutic group consisting essentially of: a cardiac resynchronization therapy parameter, a continuous positive air pressure parameter, a drug dose parameter, a drug compliance parameter, a diet compliance parameter, and a fluid intake compliance parameter.

4. The system of claim 1, wherein the at least one thoracic fluid accumulation parameter is an environmental parameter that is selected from an environmental group consisting essentially of: a posture orientation, a subject activity level, and an altitude level.

5. The system of claim 1, wherein the predicted occurrence of impending thoracic fluid accumulation is computed, at least in part, using stored weighting factors, and wherein each weighting factor corresponds to a different one of the at least one thoracic fluid accumulation parameter.

6. The system of claim 5, wherein a first weighting factor corresponding to a first thoracic fluid accumulation parameter depends on which at least one other thoracic fluid accumulation parameter is also being used to predict the occurrence of impending thoracic fluid accumulation.

7. The system of claim 5, wherein a first weighting factor corresponding to a first thoracic fluid accumulation parameter depends on how many other thoracic fluid accumulation parameters are also used to predict the occurrence of impending thoracic fluid accumulation.

8. The system of claim 1, wherein the one or more thoracic fluid accumulation prediction criteria is derived using one or more past observation of an occurrence of thoracic fluid accumulation in a subject from whom the at least one thoracic fluid accumulation parameter is sensed or received.

9. The system of claim 1, wherein the one or more thoracic fluid accumulation prediction criteria is derived using one or more past observation of an occurrence of thoracic fluid accumulation in at least one subject other than a subject from whom the at least one thoracic fluid accumulation parameter is sensed or received.

10. The system of claim 1, wherein the one or more thoracic fluid accumulation prediction criteria is entered into an external user interface.

11. The system of claim 1, further comprising a therapy control module, adapted to adjust or initiate a therapy using the predicted occurrence of impending thoracic fluid accumulation.

12. The system of claim 1, wherein the parameter collection device includes one or more of: a sensing module, an internal sensor module, a communication module, an external sensor module, an external user interface, an external communication repeater, an Internet connection, and a computerized medical database, wherein the sensing module, the internal sensor module, and the communication module are coupled to a controller, and wherein the external sensor module, the external user interface, the external communication repeater, the Internet connection, and the computerized medical database are communicatively coupled to the communication module.

13. The system of claim 1, wherein the at least one thoracic fluid accumulation parameter is a physiologic parameter comprising a cardiac chamber pressure.

14. The system of claim 1, wherein the at least one thoracic fluid accumulation parameter is a physiologic parameter comprising a cardiac output.

15. The system of claim 1, wherein the at least one thoracic fluid accumulation parameter is a physiologic parameter comprising a cardiac dimension.

16. The system of claim 1, wherein the at least one thoracic fluid accumulation parameter is a physiologic parameter comprising at least one cardiac arrhythmia.

17. The system of claim 1, wherein the at least one thoracic fluid accumulation parameter is a physiologic parameter comprising a pulmonary vein pressure.

18. The system of claim 1, wherein the at least one thoracic fluid accumulation parameter is a physiologic parameter comprising a blood drug concentration.

19. The system of claim 1, wherein the at least one thoracic fluid accumulation parameter is a physiologic parameter comprising a respiratory rate.

20. The system of claim 1, wherein the at least one thoracic fluid accumulation parameter is a physiologic parameter comprising a tidal volume.

21. The system of claim 1, wherein the at least one thoracic fluid accumulation parameter is a physiologic parameter comprising a breathing sleep disorder.

22. The system of claim 1, wherein the at least one thoracic fluid accumulation parameter is a physiologic parameter comprising at least one night cough.

23. The system of claim 1, wherein the at least one thoracic fluid accumulation parameter is a physiologic parameter comprising at least one heart sound.

24. The system of claim 1, wherein the at least one thoracic fluid accumulation parameter is a physiologic parameter comprising at least one lung sound.

25. The system of claim 1, wherein the at least one thoracic fluid accumulation parameter is a physiologic parameter comprising a blood gas concentration.

26. The system of claim 1, wherein the at least one thoracic fluid accumulation parameter is a physiologic parameter comprising a blood electrolyte level.

27. The system of claim 1, wherein the at least one thoracic fluid accumulation parameter is a physiologic parameter comprising and a neurohormone level.

28. The system of claim 1, wherein the at least one thoracic fluid accumulation parameter is a therapeutic parameter.

29. The system of claim 1, further comprising an implantable medical device including one or more sensors and adapted to sense the at least one thoracic fluid accumulation parameter that is statistically associated with impending thoracic fluid accumulation.

30. The system of claim 1, wherein the probability assertion associated with the at least one thoracic fluid accumulation parameter is derived from past observations of instances in which the at least one thoracic fluid accumulation parameter occurs alone or together with a thoracic fluid accumulation within a specified time period.

* * * * *